(12) United States Patent
Feagin et al.

(10) Patent No.: US 12,258,558 B2
(45) Date of Patent: Mar. 25, 2025

(54) COMPOSITIONS AND METHODS FOR SCREENING APTAMERS

(71) Applicants: CZ Biohub SF LLC, San Francisco, CA (US); The Board of Trustees of the Leland Stanford Junior University, Stanford, CA (US)

(72) Inventors: Trevor Feagin, Stanford, CA (US); Diana Wu, Stanford, CA (US); Peter Mage, Stanford, CA (US); John Coller, Stanford, CA (US); Hyongsok Tom Soh, San Francisco, CA (US)

(73) Assignees: CZ Biohub SF, LLC, San Francisco, CA (US); The Board of Trustees of The Leland Stanford Junior University, Stanford, CA (US)

( * ) Notice: Subject to any disclaimer, the term of this patent is extended or adjusted under 35 U.S.C. 154(b) by 1055 days.

(21) Appl. No.: 15/734,512

(22) PCT Filed: Jun. 4, 2019

(86) PCT No.: PCT/US2019/035345
§ 371 (c)(1),
(2) Date: Dec. 2, 2020

(87) PCT Pub. No.: WO2019/236548
PCT Pub. Date: Dec. 12, 2019

(65) Prior Publication Data
US 2021/0324374 A1    Oct. 21, 2021

Related U.S. Application Data

(60) Provisional application No. 62/680,435, filed on Jun. 4, 2018.

(51) Int. Cl.
*C12N 15/10* (2006.01)
*C40B 30/04* (2006.01)

(52) U.S. Cl.
CPC .......... *C12N 15/1048* (2013.01); *C40B 30/04* (2013.01)

(58) Field of Classification Search
None
See application file for complete search history.

(56) References Cited

U.S. PATENT DOCUMENTS

| 2006/0121489 A1 | 6/2006 | Gorenstein et al. |
| 2008/0020939 A1 | 1/2008 | Stanton et al. |

(Continued)

FOREIGN PATENT DOCUMENTS

| WO | 2008073856 A2 | 6/2008 |
| WO | 2014082083 A1 | 5/2014 |
| WO | 2015049356 A1 | 4/2015 |

OTHER PUBLICATIONS

Wang et al., "Multiparameter Particle Display (MPPD): A Quantitative Screening Method for the Discovery of Highly Specific Aptamers," Angew. Chem. Int. Ed. 2017, 56:744-747. (Year: 2017).*

(Continued)

*Primary Examiner* — Kaijiang Zhang
(74) *Attorney, Agent, or Firm* — Kilpatrick Townsend & Stockton LLP

(57) ABSTRACT

The disclosure is directed to methods and compositions for screening a library of aptamers for aptamers having a binding affinity to a target molecule. The methods and compositions described herein utilize a throughput approach that is able to simultaneously measure binding affinity and link the binding affinity to the identity (e.g., sequence) of the aptamer.

24 Claims, 24 Drawing Sheets

Specification includes a Sequence Listing.

1. Cluster generation and sequencing

2. Conversion to non-natural aptamers

3. Multicolor binding screen in complex background

(56) References Cited

U.S. PATENT DOCUMENTS

2011/0263459 A1* 10/2011 Borer et al. .......... C12N 15/111
  506/16
2013/0281324 A1  10/2013 Gouliaev et al.
2017/0268056 A1   9/2017 Vigneault et al.

OTHER PUBLICATIONS

Bentley et al., "Accurate whole human genome sequencing using reversible terminator chemistry," Nature 2008, 456:53-59. (Year: 2008).*
Bentley et al., "Accurate Whole Human Genome Sequencing Using Reversible Terminator Chemistry", Nature, vol. 456, No. 07517, Nov. 6, 2008, pp. 53-59.
PCT/US2019/035345, "International Search Report and Written Opinion", Oct. 28, 2019, 14 pages.
Tolle , "Click-SELEX-A Versatile Approach Towards Nucleobase-Modified Aptamers", Available Online at: http://hss.ulb.uni-bonn.de/2016/4492/4492.pdf, 2016, 149 pages.
Wang et al., "Multi-Parameter Particle Display (MPPD): A Quantitative Screening Method for Discovery of Highly Specific Aptamers", Angewandte Chemie International Edition, vol. 56, No. 3, Jan. 16, 2017, pp. 744-747.
Wang et al., "Particle Display: A Quantitative Screening Method for Generating High-Affinity Aptamers", Angewandte Chemie International Edition, 2014, pp. 4896-4901, 126.
International Search Report and Written Opinion, Application No. PCT/US2019/035378, Mailed on Nov. 13, 2019, 9 pages.

* cited by examiner

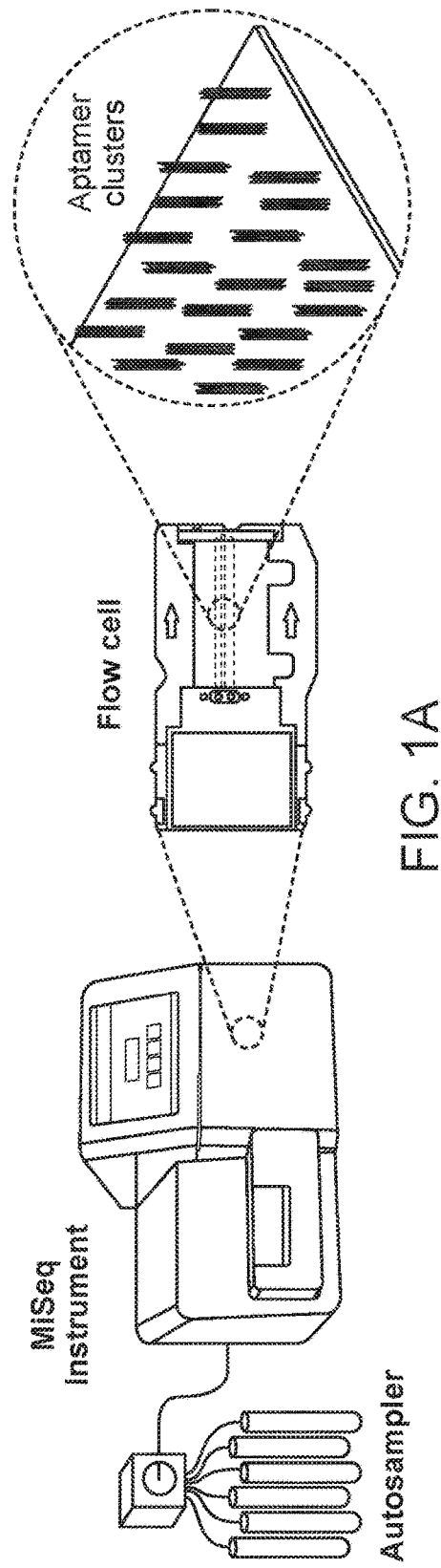
FIG. 1A
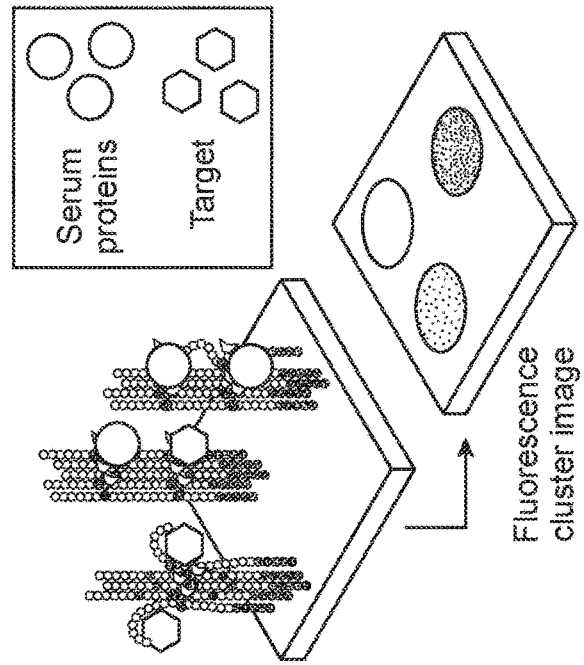
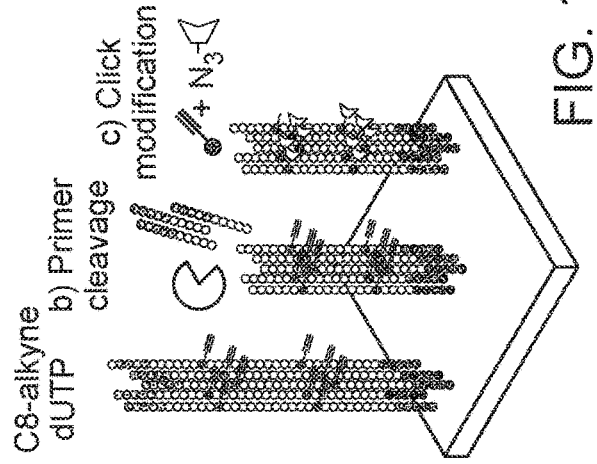
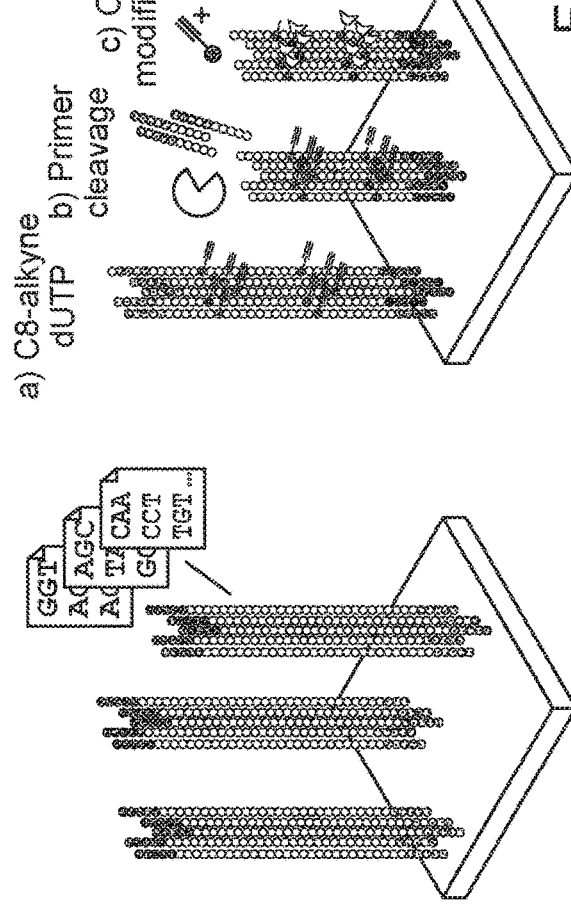
FIG. 1B

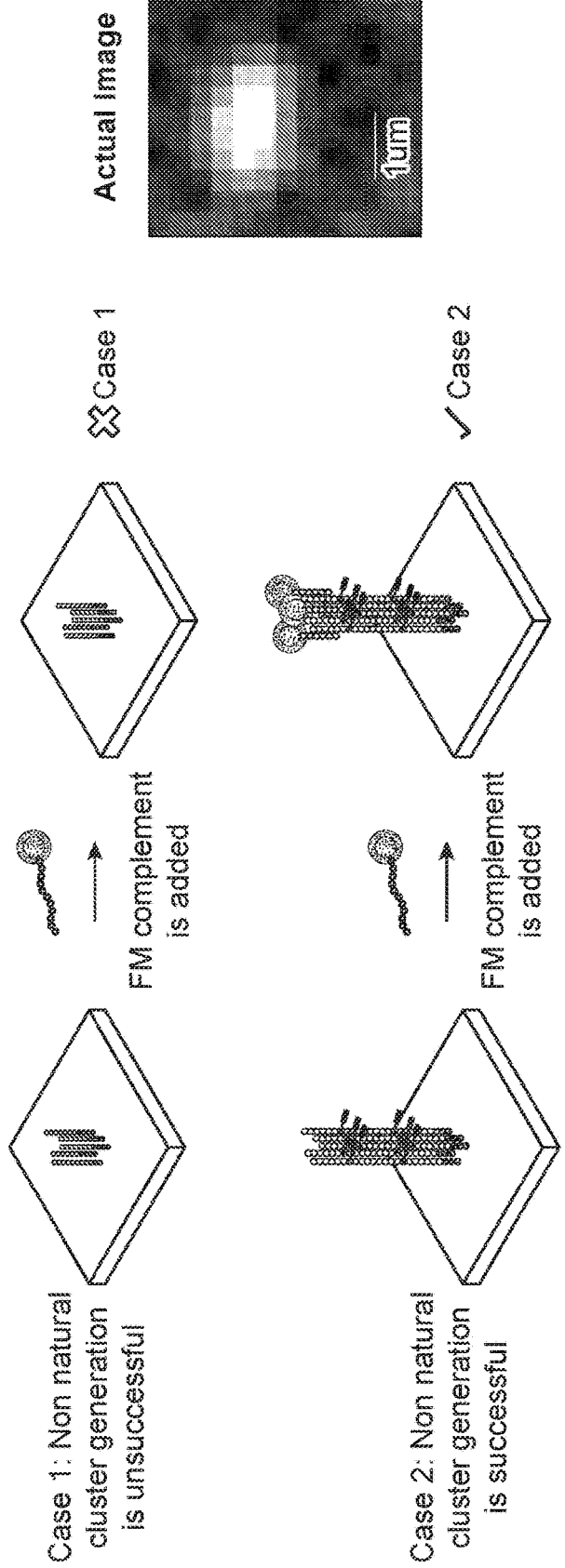
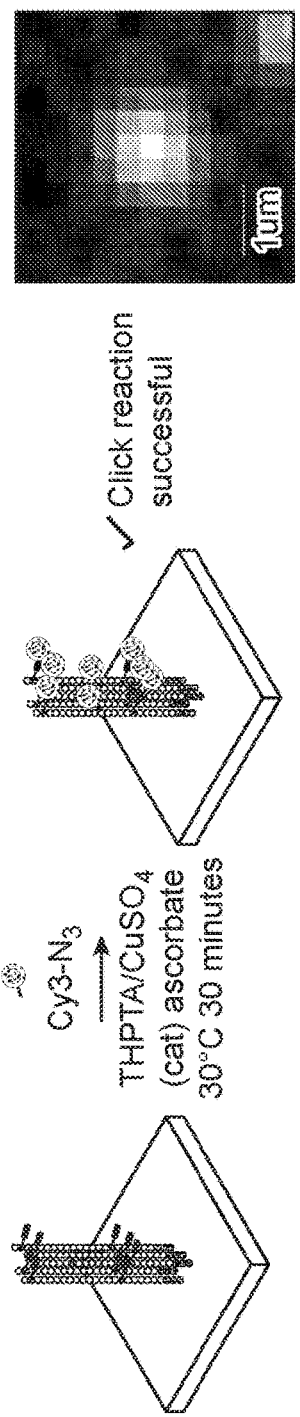
FIG. 3A
FIG. 3B

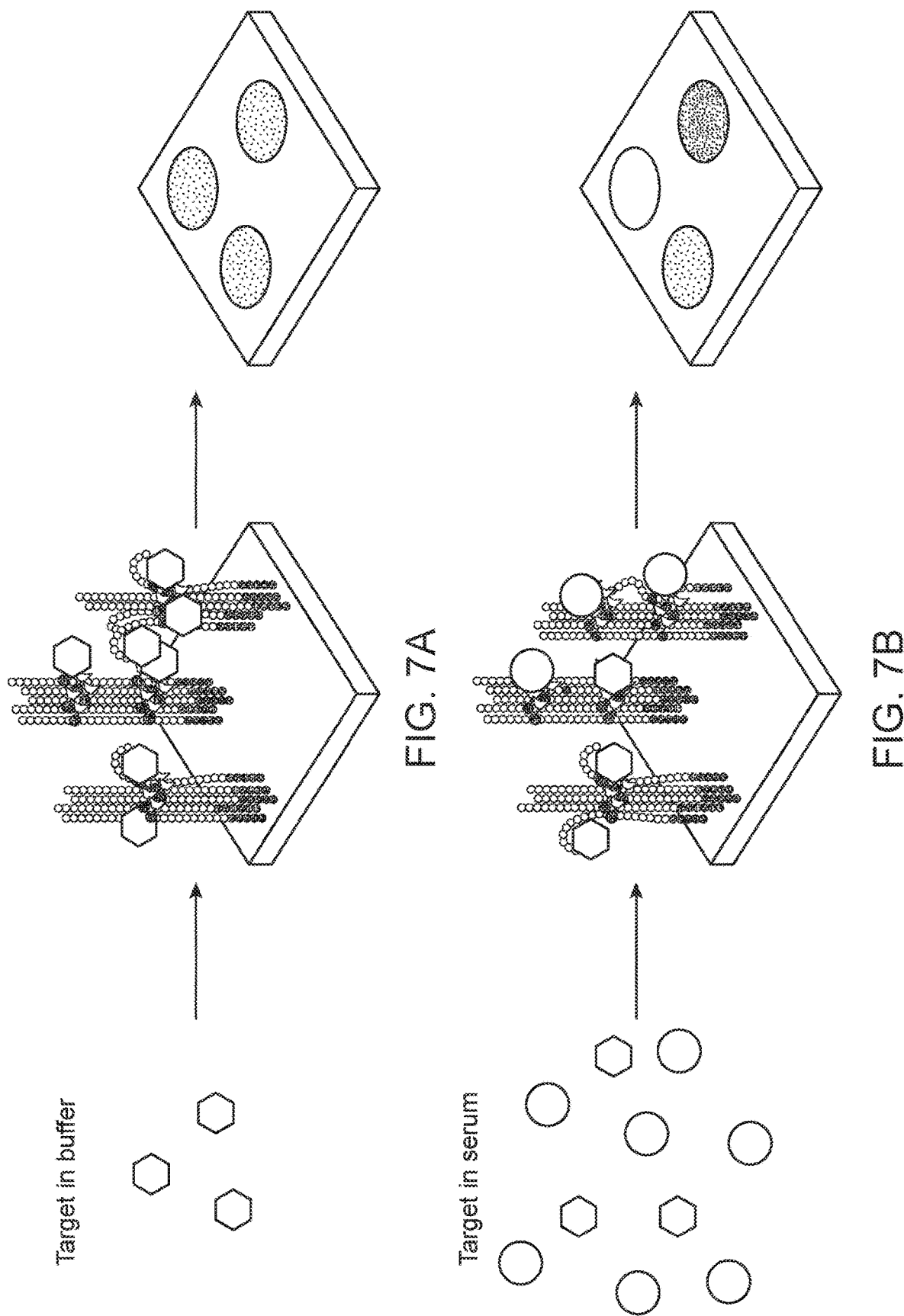

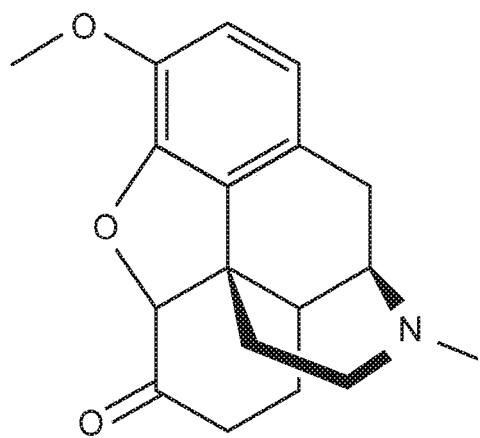
Hydrocodone
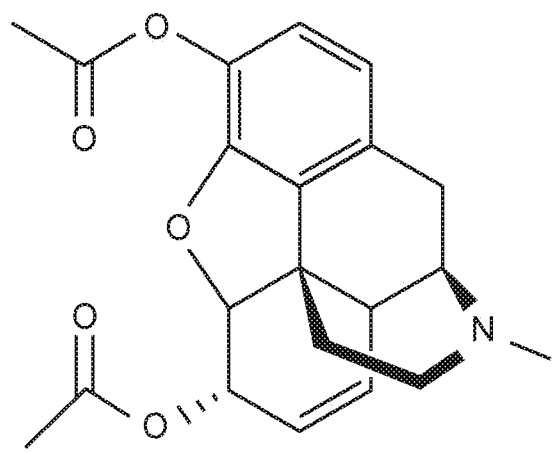
Heroin
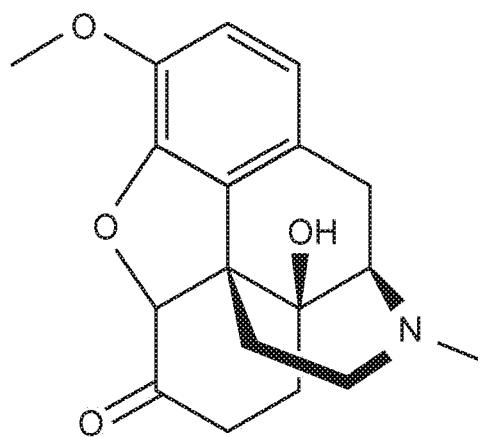
Oxycodone
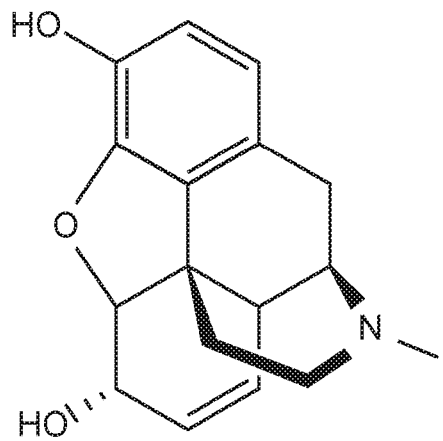
Morphine
FIG. 9

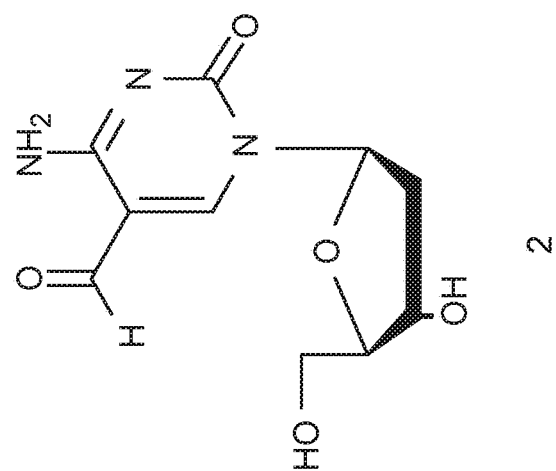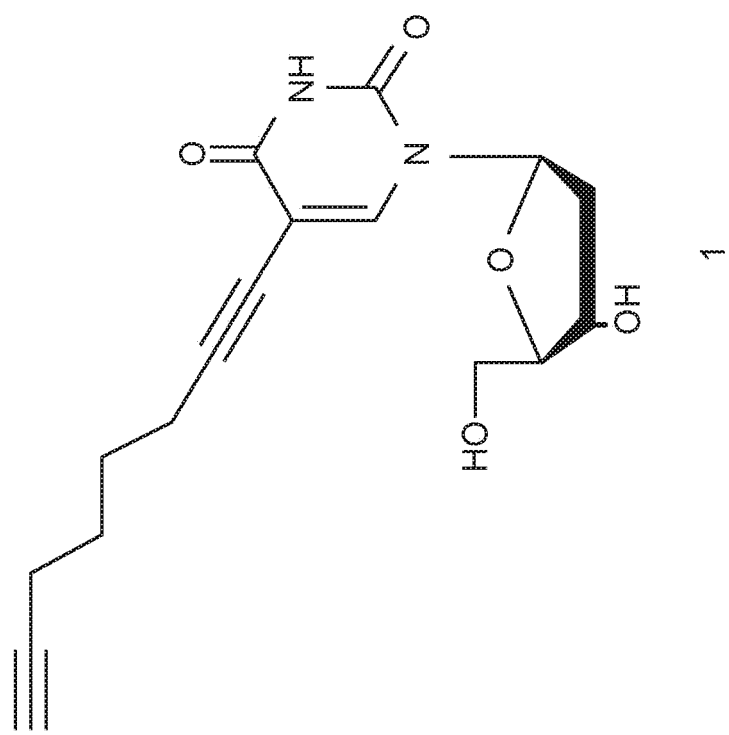
FIG. 12

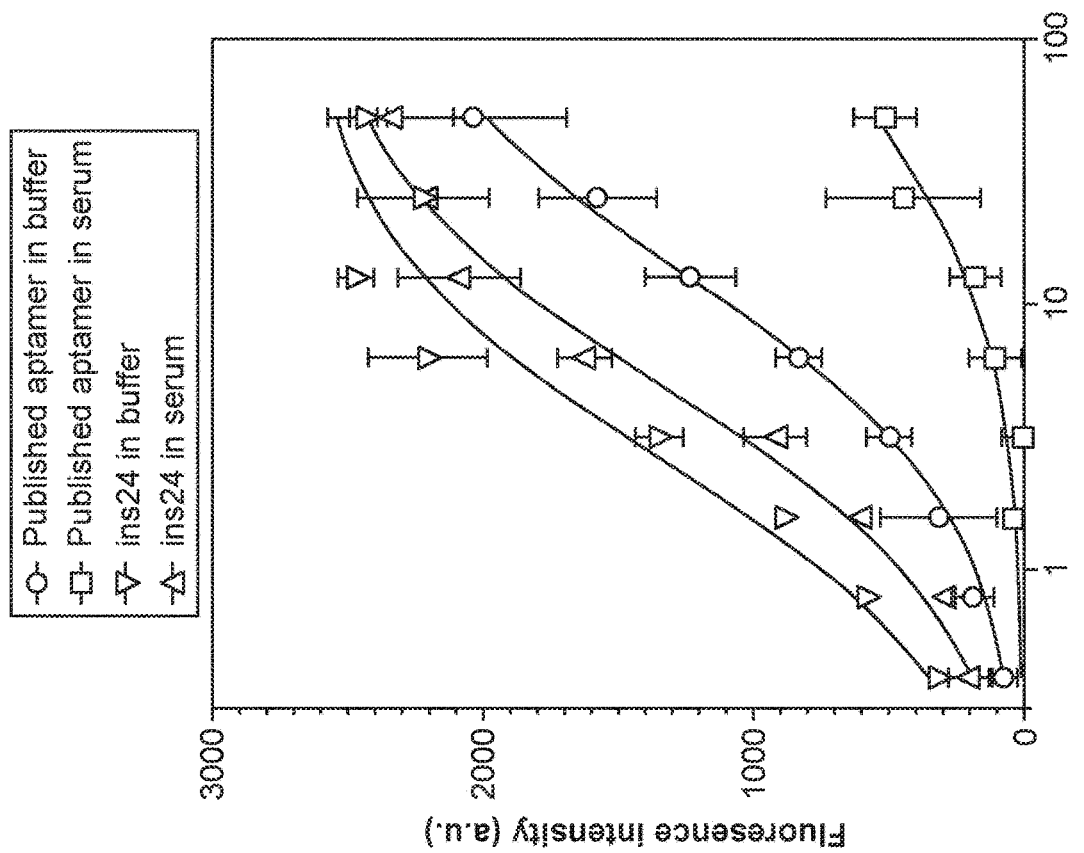
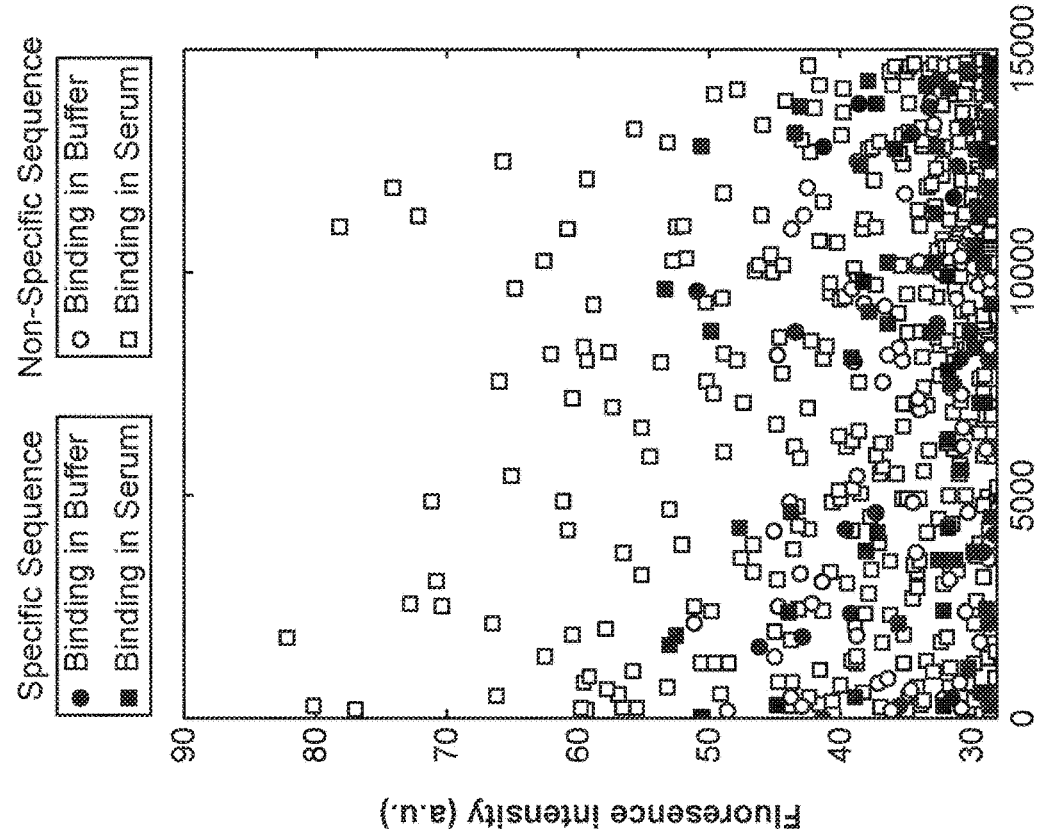

SEQUENCE LISTING

<160> NUMBER OF SEQ ID NOS: 22

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(43)
<223> OTHER INFORMATION: a, c, t, g, unknown or other

<400> SEQUENCE: 1
tcgtcggcag cgtcagatgt gtataagaga caghnnnnnn nnnagcagca cagaggtcag    60
atg                                                                 63

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtctcgtggg ctcggagatg tgtataagag acaggaattc ttcacggtag cacgcatagg    60

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agcagcacag aggtcagatg aattgggccc gtccgtatgg tgggtcctat gcgtgctacc    60
gtgaa                                                               65

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
accgacggaa cgccaaagaa acgcaagg                                       28

<210> SEQ ID NO 5
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (35)..(37)
<223> OTHER INFORMATION: a, c, t, g, unknown or other

<400> SEQUENCE: 5
tcgtcggcag cgtcagatgt gtataagaga caghnnntgg agcttggatt gatgtggtgt    60

```
gtgagtgcgg tgcccgaatt cctgtctctt atacacatct ccgagcccac gagac      115
```

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
caattgggcc cgtccgtatg gtgggt                                      26
```

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ggtggtgggg ggggttggta gggtgtcttc                                  30
```

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
cctctctatg gacacactac cct                                         23
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ctgcactgcg ttcctgatac cct                                         23
```

<210> SEQ ID NO 10
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cctctctatg gacacactac cctcccagta gggtggcagt cagggagtac ataagggtat 60
caggaacgca gtgcag                                                 76
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgcatacca gcttattcaa tt                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gccgagattg cacttactat ct                                              22

<210> SEQ ID NO 13
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgcatacca gcttattcaa tcgtcgagaa ctcctccggc tctaactccg attatagcca     60
aagatagtaa gtgcaatctc ggc                                             83

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(37)
<223> OTHER INFORMATION: a, c, t, g, unknown or other

<400> SEQUENCE: 14
tcgtcggcag cgtcagatgt gtataagaga caghnnngcg cataccagct tattcaatt      59

<210> SEQ ID NO 15
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtctcgtggg ctcggagatg tgtataagag acaggaattc gccgagattg cacttactat     60
ct                                                                    62

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 agccga                                                                 6

<210> SEQ ID NO 17
<211> LENGTH: 6

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 cgttcg                                                                    6

<210> SEQ ID NO 18
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 gttatc                                                                    6

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atgaagccgc ccgaacgtgc ccatgacccc tgcctatcgc                               40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
accgaccggt taacacaacg aaatacgcgg tatccatcat                               40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gggcccgtag aattggaaaa tattaccttc cggaaggcaa                               40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
accgtcgaga actcctccgg ctctaactcc gattatagcc                               40
```

COMPOSITIONS AND METHODS FOR SCREENING APTAMERS

REFERENCE TO RELATED APPLICATIONS

This application is a 371 application and claims the benefit of PCT Application No. PCT/US2019/035345, filed Jun. 4, 2019, which claims benefit of U.S. Provisional Patent Application No. 62/680,435, filed Jun. 4, 2018, which applications are incorporated herein by reference in their entirety.

FEDERALLY SPONSORED RESEARCH AND DEVELOPMENT

This invention was made with Government support under contract N66001-14-2-4055 awarded by the Defense Advanced Research Projects Agency, under contract N66001-16-2-4063 awarded by the Defense Advanced Research Projects Agency and under contracts GM129313 and OD025342 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 3, 2019, is named 103182-1137212-000610WO_SL.txt and is 6,226 bytes in size.

BACKGROUND OF THE DISCLOSURE

Since the invention of monoclonal antibodies in 1975, affinity reagents that specifically bind to their target molecules have revolutionized biology and medicine. In addition to antibodies generated through the hybridoma process, there are now many other types of synthetic affinity reagents that are discovered through in vitro screening techniques including phage display [1], yeast display [2], mRNA display [3] and others [4]. DNA and RNA aptamers are a highly useful class of synthetic affinity reagents, but their performance can be greatly improved through the site-specific incorporation of "non-natural", chemically-modified nucleotides [5]-[7]. These non-natural aptamers possess a far greater chemical repertoire than the can be achieved with the four nucleotides that comprise natural aptamers, creating the potential for far superior target affinity and specificity. Several groups have made important progress in generating aptamers using "non-natural" bases [8]. For example, Somalogic (Boulder, CO) have produced non-natural aptamers incorporating deoxyuridine triphosphate (dUTP) analogs modified at the 5-position (R), which they have modified with a wide range of functional groups including 3-indole-2-ethyl, benzyl, and 1-naphthylmethyl [6]. In addition, Holliger and co-workers have produced aptamers incorporating six different non-natural nucleotides, in which the canonical ribofuranose ring of DNA and RNA is replaced by five- or six-membered congeners, such as 1,5-anhydrohexitol nucleic acids (HNAs) or cyclohexenyl nucleic acids (CeNAs) [7]. These aptamers exhibit excellent affinity and specificity for protein targets in clinical samples, greatly exceeding that of natural DNA and RNA aptamers [9]. Non-natural aptamers also offer the exciting potential for targeting molecules for which the generation of monoclonal antibodies remains difficult, such as small-molecule drugs, metabolites, and carbohydrates [10]. These non-natural aptamers have also been proven to be extraordinarily stable [11], [12] and are considerably less expensive than monoclonal antibodies [13]. Finally, since they are sequence-defined and chemically synthesized, non-natural aptamers exhibit highly reproducible performance and can be distributed as sequence information rather than as a physical entity.

Unfortunately, the process of generating non-natural aptamers is challenging, and limited to a few specialized laboratories. This is largely due to three key problems. First, incorporation of new chemical functional groups typically requires novel polymerases. Natural polymerases are typically tolerant to minor modifications, but stall and fail to incorporate nucleotides when challenged with more complex modifications. One can overcome this problem by engineering polymerase enzymes to enable processing of bulkier modified nucleotides [8], [14], but this is a costly, time-consuming process that must be repeated for every new modification. More importantly, it greatly restricts the extent to which researchers can explore the full chemical space that could potentially be available. Second, the selection process is labor intensive and often results in aptamers with low-specificity. Typical SELEX-style experiments require many months to generate an aptamer for a target. Furthermore, most selections are performed in buffer, to avoid unintended selection of aptamers against interferents. However, aptamers selected in buffer often exhibit poor specificity in complex samples such as cell lysate or serum [15]. Many labs perform "negative selections", but these procedures nevertheless often result in failed selections [16]-[19]. Finally, characterizing affinity and specificity is lengthy and labor intensive, greatly limiting the number of selected aptamers that can be tested. Aptamers selected in a typical SELEX experiment must be measured individually in a low-throughput manner, typically using analytical techniques such as electrophoretic mobility shift assays [20], filter-binding assays [21], flow cytometry [4], or surface plasmon resonance [22]. All of these methods require laborious titration of each aptamer with its target, meaning that characterization of individual aptamer sequences remains extremely burdensome.

BRIEF SUMMARY OF THE DISCLOSURE

In one aspect, the disclosure features a method for screening a library of aptamers for aptamers having binding affinity to a target molecule, comprising: (a) providing a solid support comprising clusters of sequence-identified adaptor end-linked aptamers, wherein each cluster comprises a plurality of identical sequence-identified adaptor end-linked aptamers comprising one or more non-natural nucleotide covalently bonded to a binding agent, and optionally extended solid support-linked oligonucleotides comprising complements of the adaptor end-linked aptamers, and wherein the sequence of the adaptor end-linked aptamers in each cluster is unique compared to that of the other clusters; (d) probing the clusters of adaptor end-linked aptamers linked to the solid support with a target molecule; (e) washing unbound target molecule from the solid support; (f) screening the solid support for binding and location of the target molecule; and (g) correlating the location of binding of the target molecule to the nucleotide sequence of an solid support-linked aptamer at the location of binding of the target molecule, thereby identifying the nucleotide sequence of an aptamer that binds the target molecule.

In some embodiments of the method, the providing comprises: (a) hybridizing a plurality of adaptor end-linked aptamers to adaptor-complementary oligonucleotides linked to a solid support; (b) subjecting the hybridized adaptor end-linked aptamers to nucleotide sequencing by: (i) extending with a polymerase the hybridized adaptor-complementary oligonucleotide in a template-dependent manner to generate an extended solid support-linked antisense oligonucleotide whose sequence is complementary to the adaptor end-linked aptamer; and (ii) generating clusters of identical solid support-linked oligonucleotides having sense and antisense strands through bridge amplification; (iii) selectively cleaving sense oligonucleotides, leaving only antisense oligonucleotides linked to the solid support; (iv) sequencing by synthesis the antisense oligonucleotides; and (v) recording the location and nucleotide sequence of the antisense oligonucleotides linked to the solid support; (c) performing bridge amplification of the antisense oligonucleotides linked to the solid support in the presence of one or more non-natural nucleotide to form clusters of extended solid support-linked sense oligonucleotides and antisense oligonucleotides, thereby introducing a non-natural nucleotide into the sense oligonucleotides wherein the non-natural nucleotide comprises a functional group to form the sequence-identified adaptor end-linked aptamers; (d) selectively cleaving the antisense oligonucleotides from the solid support, thereby providing a solid support comprising clusters of sequence-identified adaptor end-linked aptamers.

In some embodiments, the non-natural nucleotide comprises an alkyne or azide functional group. In particular embodiments, the non-natural nucleotide comprises an alkyne functional group (e.g., the non-natural nucleotide is C8-alkyne-dUTP).

In some embodiments, the method further comprises following the performing bridge amplification, modifying the non-natural nucleotide by covalently conjugating a binding agent comprising a compatible functional group to the non-natural nucleotide, wherein the compatible functional group in the binding agent and the functional group in the non-natural nucleotide react to form a modified non-natural nucleotide comprising the binding agent. In some embodiments, the compatible functional group in the binding agent is an azide.

In some embodiments, during the modifying the azide undergoes Cu-catalyzed azide-alkyne cycloaddition (CuAAC) with the alkyne in the non-natural nucleotide to form a covalent bond.

In some embodiments of the method, the binding agent is an amino acid, a sugar (e.g., a monosaccharide or a polysaccharide), a peptide (e.g., a synthetic peptide), or a protein (e.g., a synthetic protein). In some embodiments, the binding agent is an azide-modified tyrosine or an azide-modified tryptophan. In some embodiments, the binding agent is an azide-modified boronic acid.

In some embodiments of the method, the target molecule is a peptide, a protein, a small molecule (e.g., less than 1500 daltons), a mixture of cellular membrane fragments, or a microorganism. In some embodiments, the target molecule is labeled.

In some embodiments of the method, the adaptor end-linked aptamers comprise a label and the target molecule induces a conformational change in the adaptor end-linked aptamers upon binding that alters signal from the label.

In some embodiments of the method, the target molecule is in a complex mixture including non-target molecules.

In some embodiments of the method, the method further comprises performing a binding assay that measures binding affinity the adaptor end-linked aptamers to the target molecule. In some embodiments, the binding assay is a fluorescence-based binding assay.

In some embodiments of the method, the target molecule is insulin. In some embodiments, an aptamer that binds to insulin identified by the method described herein has a sequence that has at least 85% (e.g., 86%, 88%, 90%, 92%, 94%, 96%, 98%, or 100%) identity to the sequence of SEQ ID NO:13. In some embodiments, an aptamer that binds to insulin identified by the method described herein has the sequence of SEQ ID NO:13.

In some embodiments of the method, the solid support comprises a polystyrene surface, a polypropylene surface, a gold surface, a glass surface, or a silicon wafer.

In another aspect, the disclosure features a solid support comprising clusters of non-natural aptamers, wherein each cluster comprises a plurality of non-natural aptamers having the same sequence and wherein the sequence of the non-natural aptamers in each cluster is different compared to that of the other clusters, wherein the non-natural aptamer comprises at least one non-natural nucleotide.

In some embodiments of the solid support, the non-natural nucleotide comprises a functional group (e.g., an alkyne or azide functional group). In particular embodiments, the non-natural nucleotide comprises an alkyne functional group (e.g., the non-natural nucleotide is C8-alkyne-dUTP).

In some embodiments of the solid support, the non-natural nucleotide is covalently bonded to a binding agent. In particular embodiments, the non-natural nucleotide is bonded to the binding agent via a triazole moiety.

In some embodiments of the solid support, the binding agent is an amino acid, a sugar (e.g., a monosaccharide or a polysaccharide), a peptide (e.g., a synthetic peptide), or a protein (e.g., a synthetic protein). In some embodiments, the binding agent is an azide-modified tyrosine or an azide-modified tryptophan. In some embodiments, the binding agent is an azide-modified boronic acid.

In some embodiments of the solid support, the clusters are in contact with a target molecule. In some embodiments, the target molecule is a peptide, a protein, a small molecule (e.g., less than 1500 daltons), a mixture of cellular membrane fragments, or a microorganism. In some embodiments, the target molecule is labeled.

In some embodiments of the solid support, the non-natural aptamers comprise a label and a target molecule induces a conformational change in at least some of the non-natural aptamers upon binding that alters signal from the label. In some embodiments, the solid support comprises at least 100 different of said clusters.

In another aspect, the disclosure features a method for generating an aptamer library enriched for aptamers that bind a target molecule, the method comprising: generating a data set representing binding data of a target molecule to an initial library of aptamers, generating a machine learning model using the data set as a training data set that includes: for each of the aptamers of the initial library, (1) an output label of a measured affinity binding level of the target molecule to the aptamer; and (2) a set of input features comprising sequence information about the aptamer, generating with the machine learning model a new untested library of aptamers predicted to have desired binding properties for the target molecule, and testing the new untested library of aptamers for binding to the target molecule.

In some embodiments of the method, the set of input features are aptamer subsequences. In some embodiments, generating the machine learning model comprises calculating a sum of log-affinities of subsequence k-mers. In some embodiments, the subsequences are 8-10 base long. In some embodiments, generating the machine learning model comprises DeBruijn graph sampling.

In some embodiments of the method, the method further comprises generating a second data set representing binding data of a target molecule to the new untested library of aptamers, training the machine learning model using the second data set, generating with the machine learning model a second new untested library of aptamers predicted to have desired binding properties for the target molecule, and testing the second new untested library of aptamers for binding to the target molecule.

In another aspect, the disclosure features a computer program product comprising a computer-readable storage medium containing computer program code for: receiving a data set representing affinity binding data of a target molecule to an initial library of aptamers, generating a machine learning model using the data set as a training data set that includes: for each of the aptamers of the initial library, (1) an output label of a measured affinity binding level of the target molecule to the aptamer; and (2) a set of input features comprising sequence information about the aptamer, generating with the machine learning model a new untested library of aptamers predicted to have desired binding properties for the target molecule, and outputting sequences of aptamers making up the new untested library of aptamers.

In some embodiments of the computer program product, the set of input features are aptamer subsequences. In some embodiments, generating the machine learning model comprises calculating a sum of log-affinities of subsequence k-mers. In some embodiments, the subsequences are 8-10 base long. In some embodiments, generating the machine learning model comprises DeBruijn graph sampling.

Definitions

The terms "label" and "detectable label" may be used interchangeably herein to refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. Exemplary detectable moieties suitable for use as detectable labels include affinity tags and fluorescent proteins As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing.

The terms "nucleic acid", "nucleic acid sequence", "nucleic acid molecule" and "polynucleotide" may be used interchangeably herein and refer to a polymeric form of nucleotides of any length, either deoxyribonucleotides or ribonucleotides, or analogs thereof, and may include naturally occurring nucleotides and/or modified nucleotides.

Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "oligonucleotide" can refer to a polynucleotide chain, typically less than 200 residues long, most typically between 15 and 100 nucleotides long, but also intended to encompass longer polynucleotide chains. Oligonucleotides can be single- or double-stranded.

A "sequence-identified" nucleic acid means that the nucleotide sequence of the nucleic acid has been previously determined.

"Non-natural nucleotide" refers to a nucleotide that is different from the natural nucleotides of adenosine, thymidine, guanosine, cytosine, and uracil. Non-natural nucleotides will generally include a sugar molecule (e.g., a five-carbon sugar such as ribose or deoxyribose), a nitrogenous base, and a phosphate group (when a free nucleotide as a triphosphate or when incorporated into a nucleic acid a monophosphate).

"Complementary", as used herein, can refer to complementarity to all or only to a portion of a sequence. The number of nucleotides in the hybridizable sequence of a specific oligonucleotide can be such that stringency conditions used to hybridize the oligonucleotide primer can prevent excessive random non-specific hybridization. The number of nucleotides in the hybridizing portion of the oligonucleotide primer can be at least as great as the defined sequence on the target polynucleotide that the oligonucleotide hybridizes to, namely, at least 5, at least 6, at least 7, at least 8, at least 9, at least 10, at least 11, at least 12, at least 13, at least 14, at least 15, at least about 20, or from about 6 to about 10 or 6 to about 12, or 12 to about 200 nucleotides, or about 10 to about 50 nucleotides.

The term "adaptor", as used herein, refers to an oligonucleotide of known sequence, the attachment of which to a specific nucleic acid sequence or a target polynucleotide strand of interest (e.g., an oligonucleotide) enables the generation of amplification-ready products of the specific nucleic acid or the target polynucleotide strand of interest. Attachment can be achieved via amplification or other primer extension, ligation, or other methods known in the art.

BRIEF DESCRIPTION OF THE DRAWINGS

FIGS. 1A-1C: Overview of the Non-Natural Aptamer Array (N2A2) system. FIG. 1A: N2A2 transforms a DNA sequencer (e.g., Illumina MiSeq) into a non-natural aptamer discovery system. FIG. 1B: The N2A2 may automatically perform every step of the non-natural aptamer discovery process, including sequencing, click-chemistry, and affinity measurement. FIG. 1C: A computational approach may be used to identify sequence motifs that correlate with target binding, and use deep-learning algorithms to generate new aptamer libraries with enhanced performance for the next round of screening.

FIGS. 3A and 3B: Establishing conditions for non-natural aptamer generation in the N2A2. FIG. 3A: Fiducial mark (FM) sequences were used to normalize the background and help with alignment of the clusters. FM complement binding demonstrates that all clusters on the flow cell have successfully incorporated C-8-alkyne dUTP. Case 1 and Case 2 respectively show what may occur if the bridge amplification with non-natural dUTP is unsuccessful or successful, with image data shown at right. FIG. 3B: The optimized click reaction conditions were working as demonstrated by conjugating an azide-tagged Cy3 onto modified dUTPs on the flow cell.

FIG. 4A: Schematic of flow cell geometry for imaging. FIG. 4B: Built-in Illumina data pipeline for MiSeq sequencing, converting from raw cluster images to sequence information. FIG. 4C: N2A2 scheme for extracting sequence-linked cluster intensities.

FIG. 5A: Images of cluster intensity during a binding assay. The intensity of a single VEGF-1 cluster (top row) or random library cluster (bottom row) is shown. Cluster boundary is indicated by the circle.

FIG. 5B: Individual binding curves of thousands of clusters exposed to varying VEGF concentrations. 1,000 randomly selected clusters were plotted for both VEGF aptamers (green and blue) as well as the random library (red).

FIGS. 7A and 7B: Selection in complex sample matrices. The results of FIG. 7A: non-natural aptamer discovery in buffer may be compared to FIG. 7B: an equivalent assay with serum, in which increasing target concentrations may be imaged in the presence of orthogonal labeled serum to distinguish specific target binding (green), non-target binding (red) and non-specific target binding (yellow) events.

FIG. 8A: Overview of hairpin scaffold screening. A stem-forming complementary region flanks the random region of the aptamer library, with single-stranded sequences respectively labeled with primers tagged with a fluorophore and a quencher. The library forms a hairpin configuration in the absence of target, with quenched fluorescence (left). Upon incubation with a target, sequences that adopt a new conformation upon target binding will produce a fluorescent signal (right). FIG. 8B: Overview of displacement strand library screening. Library members are bound to a fluorescently-tagged complementary sequence (left); those that undergo target-induced release of this complementary strand produce a measurable decrease in fluorescence.

FIG. 9: Chemical structures of four opioids.

FIG. 12: Chemical structures of modified non-natural nucleotides.

FIG. 18A: N2A2 measurements of aptamer binding in buffer and, FIG. 18B: 1% serum. Blue lines depict average intensity of unique sequences at each concentration. Red lines are sequences that have an average intensity greater than the negative control gray zone. The gray zone reflects the mean intensity of the negative control +/−1 standard deviation.

FIGS. 19A and 19B: N2A2 produces high-specificity non-natural DNA aptamers.

FIG. 19A: N2A2 measurements of aptamer binding in buffer and 1% serum at 1 µM insulin. Circles reflect each sequence's binding signal in buffer; Squares reflect each sequence's binding signal in serum. Specific sequences, sequences which show less than 10 a.u. difference between buffer and serum performance, are colored blue and red, respectively. Nonspecific sequences are colored grey. Candidates for further testing were chosen from the red/blue sequences. FIG. 19B: A flow cytometry-based bead-binding assay for the previously published aptamer IGA3 (blue) and the best candidate aptamer (ins24, red) identified by N2A2 in buffer (dotted lines) and 1% human serum (solid lines). Only the N2A2 aptamer retains target binding in the serum background.

FIG. 21A: Fluorescence intensity of each unique sequence when modified with W (x-axis) compared to natural DNA. W is strongly preferred. FIG. 21B: Fluorescence intensity of Y modified DNA (y-axis) vs natural DNA (x axis). No observable preference at 1 nM VEGF. FIG. 21C: Fluorescence intensity of Y modified DNA (y-axis) vs W modified DNA (x axis). Sequences consistently exhibited greater binding intensity with W modification than with Y modification.

DETAILED DESCRIPTION OF THE DISCLOSURE

I. Introduction

The disclosure is directed to methods and compositions for screening a library of aptamers for aptamers having a binding affinity to a target molecule. The methods and compositions described herein utilize a throughput approach that is able to efficiently measure binding affinities of a large number of aptamers and link the binding affinity to the identity (e.g., sequence) of the aptamer.

Figure 1C:
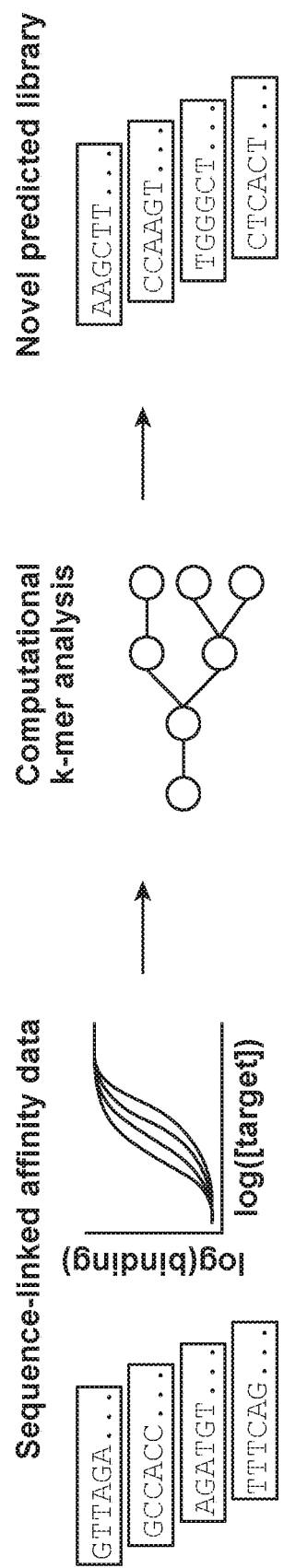
Figure 2:
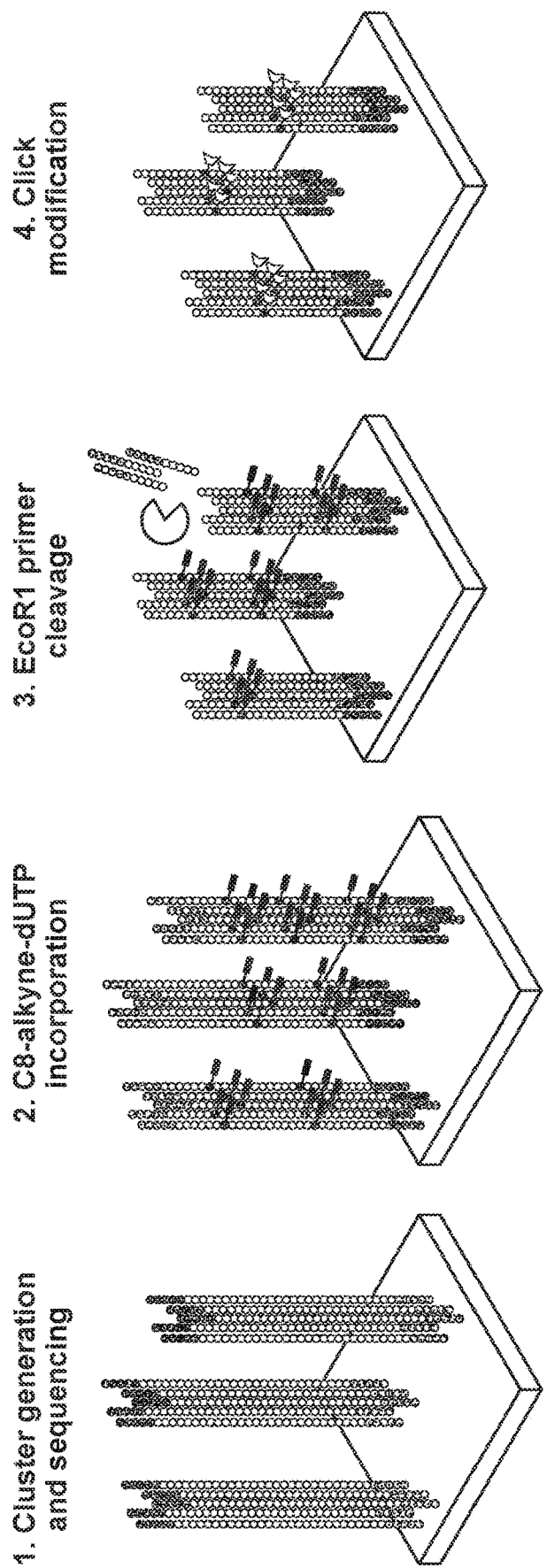
FIG. 2: Conversion of DNA into non-natural aptamers on a flow cell. Step 1) generate DNA clusters and sequence. Step 2) substitute native dTTP with C8-alkyne-dUTP to enable click conjugation. Step 3) remove bulky primer sequences that cause steric hindrance. Step 4) conjugate desired functional groups through click-chemistry.
Figures 4A, 4B:
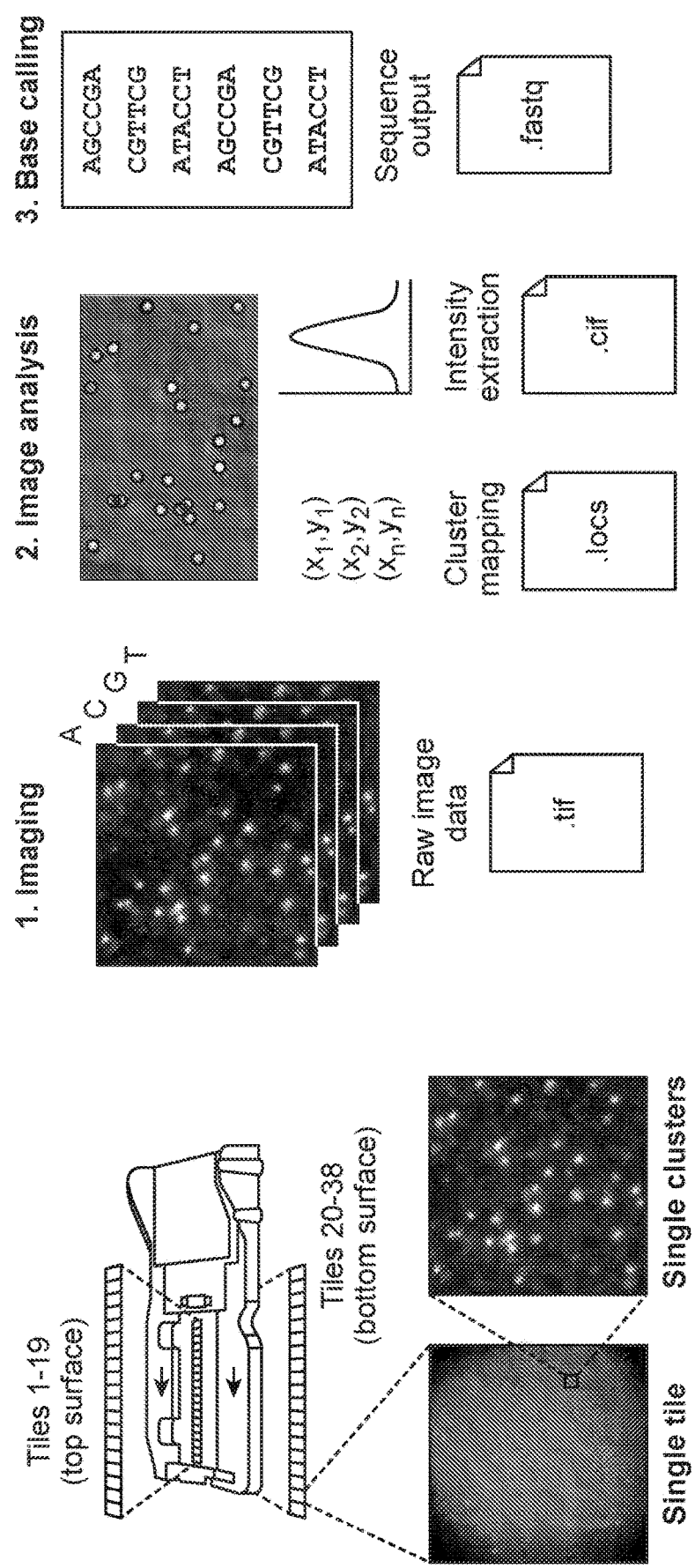
FIGS. 4A-4C: Data analysis pipeline.
Figure 4C:
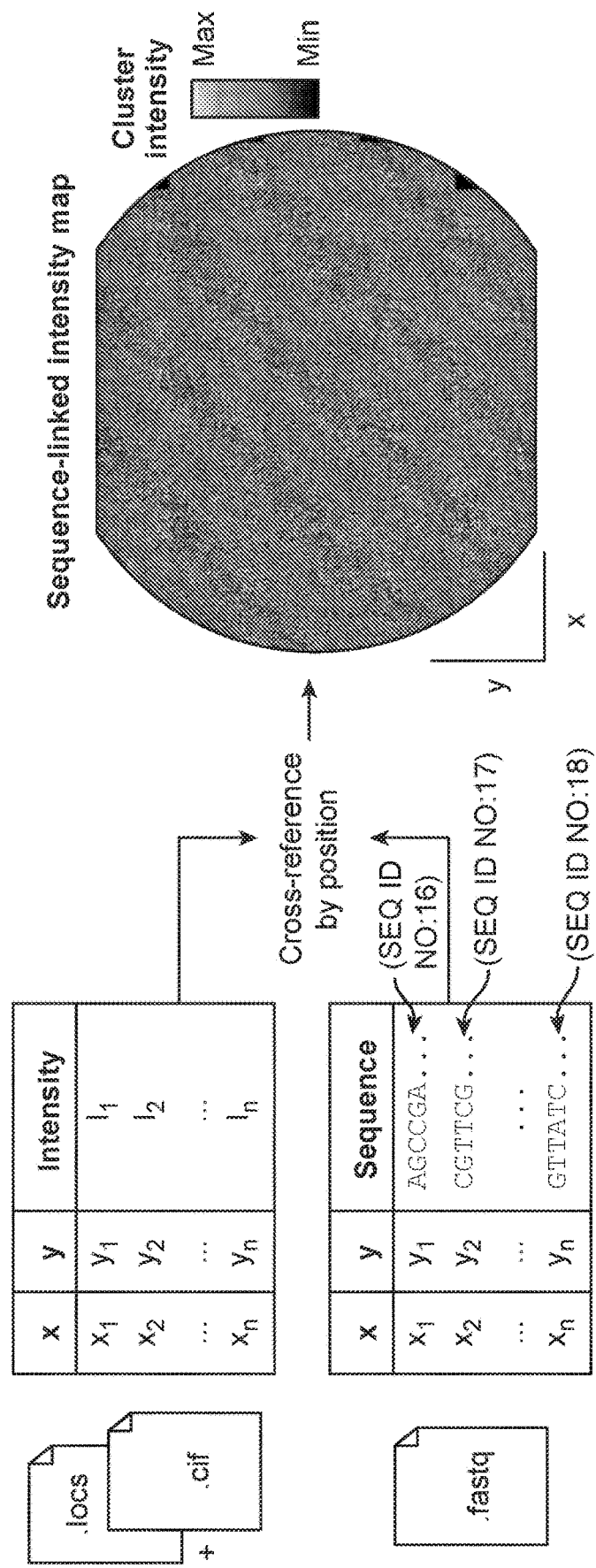

In one example, the disclosure describes the development of an integrated instrument, the Non-Natural Aptamer Array (N2A2), that enables rapid and facile aptamer discovery. In some embodiments, the N2A2 may be built on a modified version of a benchtop commercial sequencer (e.g., Illumina MiSeq). In some embodiments, the N2A2 may perform functions including sequencing, screening, and binding measurements as part of a single work-flow (FIG. 1A).

II. Screening Aptamer Clusters

The disclosure provides methods for screening a library of aptamers containing one or more non-natural nucleotide for aptamers having binding affinity to a target molecule. As described in detail further herein, the methods are able to efficiently correlate the binding signal from the target molecule to the location of the target molecule-binding adaptor or complement thereof in a flow cell.

Aptamer Cluster Generation and Sequencing

In some embodiments, the methods for screening a library of aptamers involve providing or generating clusters of aptamers or complements thereof on a solid support (e.g., a flow cell). Clusters refer to areas on a solid surface of multiple copies of the same nucleic acid linked to the same region. Each aptamer may comprise a first adaptor sequence at a first polynucleotide end, a second adaptor sequence at a second polynucleotide end, and a middle sequence. The middle sequences of different adaptors have different sequences, which will result in different aptamer sequences in different clusters. In some embodiments, the middle sequence of an aptamer may contain from 20 to 200 nucleotides (e.g., 20, 30, 40, 50, 60, 70, 80, 90, 100, 110, 120, 130, 140, 150, 160, 170, 180, 190, or 200 nucleotides). In some embodiments, each adaptor at the end of the aptamer may contain from 5 to 40 nucleotides (e.g., 5, 10, 15, 20, 25, 30, 35, 40, 45, or 50 nucleotides). In some embodiments, the first adaptor ends of the aptamers in the library are the same. Similarly, in some embodiments, the second adaptor ends of the aptamers in the library are the same, though the first adaptor sequence and the second adaptor sequences are typically different.

In some embodiments, amplification can be carried out using bridge amplification to form nucleic acid clusters on a surface. Useful bridge amplification methods are described, for example, in U.S. Pat. No. 5,641,658; US 2002/0055100; U.S. Pat. No. 7,115,400; US 2004/0096853; US 2004/0002090; US 2007/0128624; or US 2008/0009420. To generate clusters of aptamers or complements thereof by bridge amplification, the aptamers may first be hybridized to the solid support containing short polynucleotides that are complementary to the first adaptor and the second adaptor of the aptamers, i.e., one short polynucleotide that is complementary to the first adaptor and a second short polynucleotide that is complementary to the second adaptor. See, e.g., Wang et al., Nature 456 (2008), pp. 53-58. The solid support surface may be linked to a plurality of sequence-identical short polynucleotides that are complementary to the first adaptor in the aptamer, and a plurality of sequence-identical short polynucleotides that are complementary to the second adaptor in the aptamer. In some embodiments, the short polynucleotides on the surface of the solid support contain from 5 to 40 nucleotides (e.g., 5, 10, 15, 20, 25, 30, 35, 40, 45, or 50 nucleotides).

Once the aptamers are hybridized to the surface of the solid support (e.g., a planar surface, e.g., a flow cell), single-end nucleotide sequencing and amplification may be performed on the hybridized aptamers. A polymerase may be used to extend the hybridized aptamer in a template-dependent matter to generate a complement of the aptamer. Sense and antisense sequences are generated through bridge amplification. Sense oligonucleotides can be selectively cleaved from the solid support, leaving antisense oligonucleotides linked to the solid support. The antisense oligonucleotides can then be sequenced by synthesis (see, e.g., Wang et al., Nature 456 (2008), pp. 53-58.). The location on the solid support (e.g., a flow cell) and the nucleotide sequence of the adaptor and its complement may be automatically recorded. As explained more below, the aptamer sequences can subsequently be modified with non-natural nucleotides wherein known nucleotides (for example thymidine (T)) are replaced with the non-natural nucleotide. By this way, the modified aptamer sequence is determinable based on the sequence determined for the antisense oligonucleotide.

The aptamers initially hybridized to the solid support can be obtained as desired. In some embodiments, the aptamer library members are random sequences or alternatively can be previously selected physically or computationally for improve likelihood of binding the target molecule. Exemplary physically method can include for example, systematic evolution of ligands by exponential enrichment (SELEX) or other methods to enrich a random library for members that bind the target molecule. In some embodiments, several (e.g., 2, 3, 4, or more) rounds of selection occur before a selected plurality of aptamers are initially hybridized to the solid support and screened as described herein. For example, in some embodiments, a plurality of rounds of conventional SELEX may be performed to reduce the diversity of the library to a size that is amenable to sequencing (e.g., about 50-150 candidates (e.g., about 50, 60, 70, 80, 90, 100, 110, 120, 130, 140, or 150 candidates)).

In some embodiments, the solid support may be a patterned flow cell that use distinct nanowells for cluster generation to make more efficient use of the flow cell surface area. In some embodiments, a patterned flow cell may contain millions to billions of nanowells at fixed locations across the surface of the flow cell. In some embodiments, each nanowell may contain a cluster of aptamers or complements thereof generated by bridge amplification. The cluster of aptamers or complements thereof in each nanowell have the same sequence and the aptamers or complements thereof in each cluster in each nanowell is unique compared to that of the other clusters in other nanowells. The precise nanowell positioning may eliminate the need to map cluster sites and save time on each sequencing run. In some embodiments, the density of the clusters formed on the flow cell depends on the amount of aptamers loaded and the type of instrument. Different amplification and sequencing instruments may have different capacities for the ideal cluster density that generates the most high-quality data. In some embodiments, too little nucleic acid loaded may under-cluster the flow cell, which may maintain data quality at the cost of lower data output. Too much nucleic acid loaded may over-cluster the flow cell, leading to poor image resolution and data analysis problems. Depending on the instrument, nucleic acid loading density on the surface of the flow cell may be, for example, between 8 and 10 pM (e.g., 8, 8.5, 9, 9.5, or 10 pM) to reach a cluster density on the flow cell that is between 600 and 900 K/mm$^2$ (e.g., 600, 620, 740, 660, 680, 700, 720, 740, 760, 780, 800, 820, 840, 860, 880, or 900 K/mm$^2$). In some embodiments, nucleic acid loading density on the surface of the flow cell may be greater than 250 pM to reach a cluster density on the flow cell that is between 1200 and 1600 K/mm$^2$ (e.g., 1200, 1300, 1400, 1500, or 1600 K/mm$^2$). In other embodiments, nucleic acid loading density on the surface of the flow cell may be between 1 and 5 pM (e.g., 1, 2, 3, 4, or 5 pM) to reach a cluster density on the flow cell that is between 100 and 200 K/mm$^2$ (e.g., 100, 110, 120, 130, 140, 150, 160, 170, 180, 190, or 200 K/mm$^2$).

Cluster formation on the flow cell (e.g., by bridge amplification) adds short sequences to both the 3' and 5' ends of the aptamers, which in some embodiments can increase steric hindrance between the aptamer and the target. These unnecessary bases can be removed by incorporating a restriction sequence (e.g., palindromic GAATTC site) between the aptamer and the 3' sequencing primer, which can then be cleaved by the appropriate restriction enzyme (e.g., Eco-R1 nuclease for GAATTC).

In particular embodiments of the methods and compositions described herein, a non-natural nucleotide may be introduced into the aptamer or complement thereof during a subsequent amplification (e.g., bridge amplification) to create clusters of non-natural aptamers or complements thereof. For example, paired-end turnaround can be performed by which the solid support linked antisense oligonucleotides are extended by polymerase extending solid-support linked adaptors to generate sense strands in which non-natural nucleotides have been incorporated. In some embodiments, a wild-type polymerase may be able to bind and incorporate a non-natural nucleotide into the aptamer or complement thereof. In other embodiments, a polymerase may be modified or engineered to bind and incorporate a non-natural nucleotide into the aptamer or complement thereof. Examples of polymerases that may be used to perform bridge amplification are further discussed in detail herein.

In particular embodiments, the non-natural nucleotide in a non-natural aptamer may contain a functional group, which enables the non-natural aptamer to be further modified, for example with a binding agent. For example, a non-natural nucleotide may be an alkyne-modified nucleotide, for example but not limited to alkyne-modified uridine ((1) in FIG. 12), which can be further conjugated with an azide-modified molecule, such as an azide-modified binding agent. In some embodiments, the binding agent may serve the function of binding to a target molecule to bring the target molecule in proximity to the aptamer during the process of screening the aptamers for binding to the target molecule. Different functional groups that may be used in the non-natural nucleotide and the binding agent such that the binding agent can be conjugated to the non-natural aptamer are discussed in detail further herein. Exemplary binding agents can include, for example, a sugar (e.g., a monosaccharide or a polysaccharide), amino acid (e.g., a natural or non-natural amino acid; e.g., tyrosine, phenylalanine, or tryptophan), small molecule (e.g., a drug or other molecule, optionally less than 1500, 2500, or 5000 daltons), peptide (e.g., a synthetic peptide), protein (e.g., a synthetic protein), non-biological moiety, or other moieties.

A target molecule used in methods and compositions of the disclosure may be a peptide, a protein, a sugar or saccharide, a lipid, or a small molecule and in some embodiments excludes any nucleotide or polynucleotide molecules. A solution containing the target molecule may be introduced into the solid support (e.g., a flow cell) via an inlet of the solid support. A target molecule may be attached to a readable label, e.g., a fluorescent label, such that the signal from the aptamer-bound target molecule, along with its location on the solid support, may be read and recorded. In other embodiments, the target molecule may not contain a readable label. In such scenarios, the aptamers in a library to be screened may have certain scaffolds (e.g., hairpin scaffold and displacement strand) that change their structures upon aptamer binding to the target molecule. The conformational change induced by target molecule binding may in turn generate a readable signal (for example due to FRET interactions) to be recorded along with its position on the solid support. In some embodiments, the flow cell may be imaged using fluorescent microscopy.

Conformational aptamer binding can be useful, for example, when labeling a target perturbs the targets shape or ability to be recognized by an aptamer. Label-free generation of aptamers may utilize a scaffold-library that changes its structure upon binding to the target molecule. A variety of library architectures have been presented in the literature (e.g., D. P. Morse, *Biochem. Biophys. Res. Commun.*, vol. 359, pp. 94-101, 2007; S. G. Trevino and M. Levy, *Chembiochem*, vol. 15, no. 13, pp. 1877-81, September 2014; R. Stoltenburg, N. Nikolaus, and B. Strehlitz, *J. Anal. Methods Chem.*, vol. 2012, 2012; F. Pfeiffer and G. Mayer, *Front. Chem.*, vol. 4, no. June, pp. 1-21, 2016) including the "hairpin scaffold" and "displacement strand" libraries. In some embodiments, both formats may be used in parallel to perform selections, allowing for a direct comparison of the two library designs.

Figure 8B:
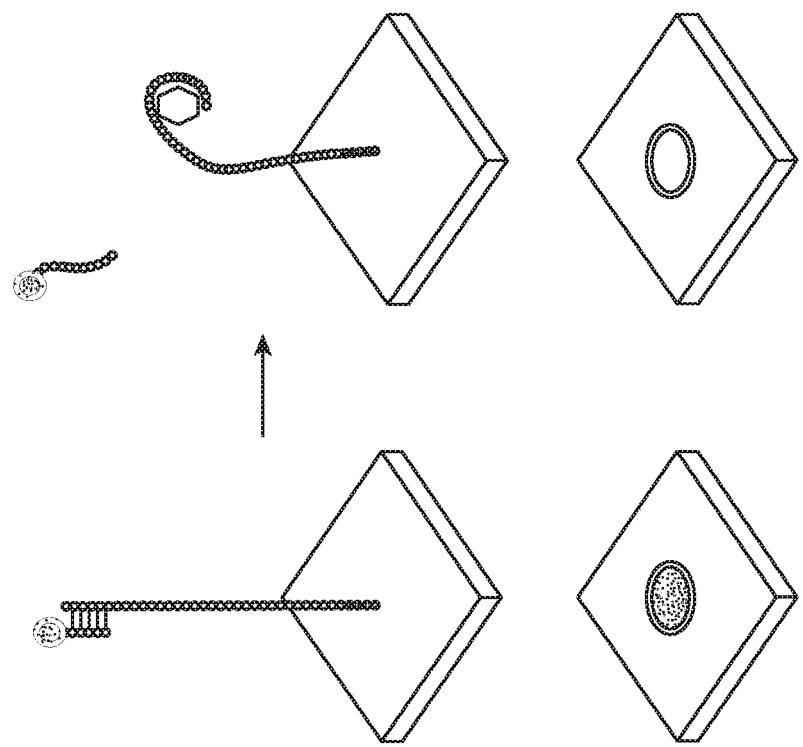
FIGS. 8A and 8B: Two structure-switching architectures for label-free screening of small-molecule aptamers.
Figure 8A:
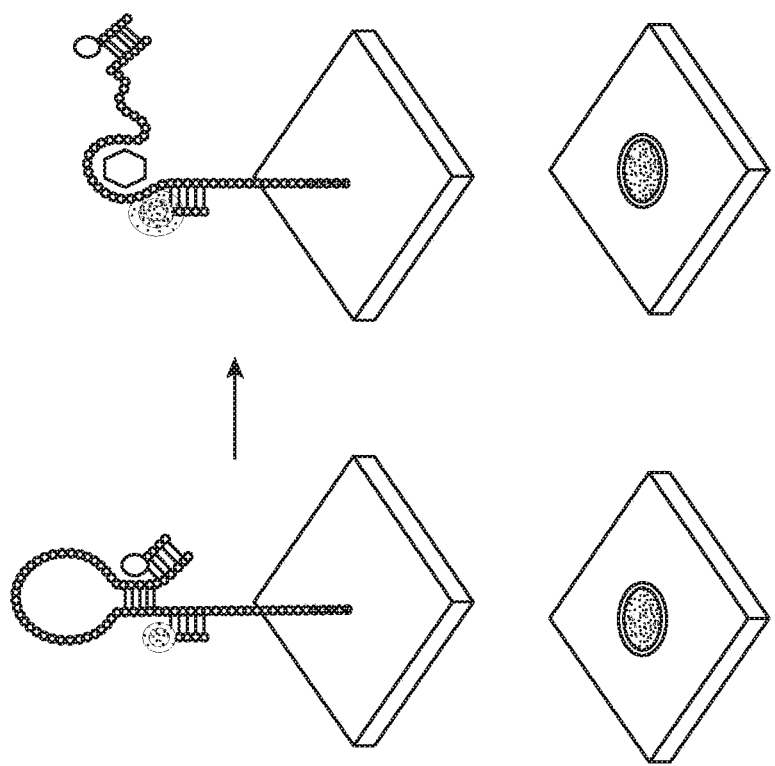

The design of the hairpin library depicted in FIG. 8A incorporates a forward primer, stem structure, a random region (30 nt), and a reverse-primer complementary sequence. During screening, a Förster resonance energy transfer (FRET) donor (e.g., fluorescein; FAM) labeled reverse primer and a forward primer complementary sequence with a FRET acceptor (e.g., a quencher dye) may be hybridized onto the sequence-defined aptamer library attached to the flow cell. In the absence of target, the library remains in a folded state, holding the quencher and donor dyes in a FRET configuration that quenches fluorescence. Target binding disrupts the stem structure, separating donor and quencher and producing a fluorescence signal. This increased donor intensity allows the direct quantification of target binding for individual aptamers simultaneously.

A displacement strand library (see, e.g., FIG. 8B) can incorporates a forward primer, a random region (e.g., 30 nt), and a reverse primer complementary sequence. The library may be incubated with a donor-labeled reverse primer and the target molecule at the same time. Only the library members that can simultaneously bind to the target and inhibit the binding of the donor labeled reverse primer produce a 'signal-off' fluorescence change.

In another alternate not requiring a labeled target molecule, an alternative "signal on" displacement strand library architecture (see, e.g., H. Qu, et al., *ACS Nano*, vol. 10, no. 10, pp. 7558-65, 2016.) may be tested. Specifically, a 3' fluorophore may be covalently incorporated onto the library via a common enzymatic process utilizing the terminal transferase enzyme. Then the flow cell may be incubated with a short, quencher-labeled displacement strand and the target may be introduced. Only sequences that undergo a target-induced conformational change may release the quencher strand and produce an increase in fluorescence.

Once the location of clusters of aptamers binding the target molecule is determined, the determined sequence of the cluster at that same location provides the sequence of the aptamer having binding activity. Thus, binding activity and sequence information for the aptamers can be efficiently correlated and determined.

In some embodiments, a set of data analysis tools can be used to link the sequence of non-natural aptamer clusters on the flow cell with its binding affinity. In some embodiments, the flow cell is organized into "tiles", each of which contains a plurality (e.g., hundreds of thousands) of DNA clusters. To the extent the method is performed on a modified Illumina or similar sequencing device, tiles on the flow cell can be analyzed by modifying the built-in imaging system to measure the fluorescence intensity of clonal aptamer clusters.

Initially, the internal binary files may be extracted by the MiSeq or other existing software during its image analysis process. These files are generated through the MiSeq's internal algorithm, which performs background normalization and Gaussian intensity fitting to convert raw cluster images to mapped cluster intensities. The files may be organized into ".locs" files, which contain the unique physical address of each cluster (expressed as the cluster's tile on the flow cell and the cluster's x/y-coordinates on that tile), and ".cif" files, which contain the extracted fluorescence intensity of each cluster in each of the four fluorescence channels. Together, these files provide an intensity map of every cluster on the flow cell. A second step in the data analysis pipeline entails extracting the tile and x/y-coordinates for each sequence as provided in the output files using the FASTQ format. In this way, both sequence and location information for each cluster on the flow cell may be obtained. Finally, the intensity map from the .locs and .cif files may be cross-referenced with the sequence smap obtained from the FASTQ file in order to create a linked sequence-intensity map. Since each cluster on the flow cell has a unique physical location, this can provide the ability to generate a 1:1 map between cluster intensities and cluster sequences, yielding a direct link between an aptamer's sequence data and its intensity at a given target concentration. By analyzing an aptamer cluster's intensity profile across a range of target concentrations, the aptamer's binding (e.g., binding affinity) may be determined.

In some embodiments the presence or absence of binding is detected. For example, a threshold binding signal can be established such that higher signal than the threshold indicates binding at a particular cluster. In some embodiments, binding affinity of the target molecule is determined for clusters. In these embodiments, different concentrations of target molecule are probed against the clusters and binding curves are generated for each cluster, thereby allowing for determination of binding affinity. Alternatively, binding specificity can be determined and selected by identifying aptamers that bind to a target molecule but do not significantly (or have reduced binding) to a non-target molecule (e.g., an isoform of the target or a molecule similar but not identical to the target molecule). For example, the methods described herein enable the binding affinity (Kd) of every aptamer to be obtained directly in the flow cell in complex samples, for example such as cell lysate and serum. This may be achieved by labeling the target and background proteins with distinct fluorophores, such that the on- and off-target binding of every aptamer can be characterized individually.

The methods described herein can be used to identify aptamers that bind to a target molecule in a complex mixture. In some embodiments, the target molecule is labeled with a first (e.g., fluorescent) label and one or more non-target molecules in the mixture are labeled with a second label that is distinguishable from the first label. In this configuration, one can select for aptamers that bind to the target molecule but do not bind to the non-target molecules (as determined by lack of signal from the second label). In some embodiments, the mixture is a complex mixture, for example a cell lysate, in which a fraction of the non-target molecules in the mixture have been labeled with the second label. In some embodiments, a non-target molecule in the mixture is similar but not identical to the target, for example is an isoform or a protein differing from the target by a post-translational modification. Alternatively, in some embodiments, one can screen for aptamers that bind to similar molecules, for example more than one members of a receptor family.

To generate aptamers that can specifically bind to the target molecule in serum, in some embodiments, a screening approach as described in, e.g., Wang et al., *Angew. Chemie Int. Ed.* vol. 94305, pp. 744-747, 2017, may be used. Briefly, the target and serum proteins may be labeled with two different-colored fluorophores. The intensity of both fluorophores at each non-natural aptamer cluster may be quantitatively measured. A naïve DNA library for binding to bead-immobilized target may be pre-enriched during positive selection. Several rounds of negative selection against bead-immobilized non-target (for example human serum) may be performed to reduce the number of sequences that bind nonspecifically to non-targets. Next, the screening methods on the solid support can be performed. For example, a control screen against target in buffer, in a titration series with the target protein labeled with a first fluorophore (FIG. 7A) may be first performed. Next, an identical titration series may be performed, except with labeled target diluted into second fluorophore (different from first fluorophore) shotgun-labeled 10% human serum. Labeling may be accomplished, for example, using active ester protein labeling kits. This dual-labeling scheme makes it possible to isolate only the aptamers that specifically bind to target but not to non-target molecules in the negative screen, as any clusters that also bind to the orthogonally labeled background fluoresce in both channels and can be avoided.

Selection in complex backgrounds introduces several challenges. The entire aptamer library might exhibit high levels of non-specific binding to background proteins. To address this, in some embodiments, several rounds of negative selection may be performed in a pre-enrichment step against bead-immobilized non-target complex mixtures, collecting only sequences that do not bind these background non-targets for further screening on the solid support as described herein. The background percentage may also be adjusted to find the maximum that allows for successful screening. This may be accomplished by holding the labeled target concentration constant and titrating in increasing concentrations (e.g., 1, 3, 5, 7, and 10%) of shotgun-labeled background. This may define the maximum working range for complex background target selection.

III. Polymerases and Non-Natural Nucleotides

In some embodiments, methods and compositions described herein comprise non-natural aptamers in which each non-natural aptamer contains at least one non-natural nucleotide. Non-natural nucleotides may be introduced into aptamers for example by a polymerase during bridge amplification as explained above.

Polymerases

Polymerases may tolerate minor modifications in certain nucleotides. In some embodiments, polymerases may also be engineered to enable processing of modified or non-natural nucleotides. Polymerases may be used for nucleic acid amplification and/or sequencing applications, including real-time applications, e.g., in the context of amplification or sequencing that include incorporation of non-natural nucleotides into DNA or RNA by the polymerase.

In some instances, the methods and compositions described herein include polymerases that incorporate non-natural nucleotides into a growing template copy, e.g., during aptamer amplification. In some embodiments, the polymerase can be modified such that the active site of the polymerase is modified to reduce steric entry inhibition of the non-natural nucleotide into the active site. In some embodiments, the polymerase may be modified to improve charge-charge or hydrophobic interactions between the non-natural nucleotide and the polymerase. In some embodiments, polymerases can be modified to accommodate one or more non-natural features of the non-natural nucleotides. Polymerases can be modified using methods pertaining to protein engineering. For example, molecular modeling can be carried out based on crystal structures to identify the locations of the polymerases where mutations can be made to modify a target activity. A variety of polymerases may be used in a method or composition set forth herein including, for example, protein-based enzymes isolated from biological systems and functional variants thereof. Reference to a particular polymerase (e.g., KOD-XL polymerase) will be understood to include functional variants thereof unless indicated otherwise. In some embodiments, a polymerase is a wild-type polymerase. In some embodiments, a polymerase is a modified, or mutant, polymerase. In some embodiments, a modified polymerase has a modified nucleotide binding site. In some embodiments, a modified polymerase has a specificity for a non-natural nucleotide (e.g., a non-natural nucleotide containing a modified base) that is at least about 10%, 20%, 30%, 40%, 50%, 60%, 70%, 80%, 90%, 95%, 97%, 98%, 99%, 99.5%, or 99.99% the specificity of the wild-type polymerase toward the natural nucleotide.

Nucleic acid polymerases generally useful in the methods described herein include DNA polymerases, RNA polymerases, reverse transcriptases, and mutant or altered forms thereof. DNA polymerases and their properties are described in detail in, among other places, DNA Replication 2nd edition, Kornberg and Baker, W. H. Freeman, New York, N.Y. (1991). Examples of DNA polymerases useful in the disclosure include, but are not limited to, *Pyrococcus furiosus* (Pfu) DNA polymerase, *Pyrococcus woesei* (Pwo) DNA polymerase, *Thermus thermophilus* (Tth) DNA polymerase, *Bacillus stearothermophilus* DNA polymerase, *Thermococcus litoralis* (Tli) DNA polymerase, 9° Nm™ DNA polymerase, Thermo Sequenase® (Amersham Pharmacia Biotech UK), Terminator™ (New England Biolabs), *Thermotoga maritima* (Tma) DNA polymerase, *Thermus aquaticus* (Taq) DNA polymerase, *Pyrococcus kodakaraensis* KOD DNA polymerase, JDF-3 DNA polymerase (from *Thermococcus* sp. JDF-3), *Pyrococcus* GB-D (PGB-D) DNA polymerase, UlTma DNA polymerase (from thermophile *Thermotoga maritima*), Tgo DNA polymerase (from *Thermococcus gorgonarius*), *E. coli* DNA polymerase I, T7 DNA polymerase, and archaeal DP1I/DP2 DNA polymerase II. Further, particular examples of thermophilic DNA polymerases include, but are not limited to, ThermoSequenase®, 9° Nm™, Terminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase.

In some embodiments, the polymerase may be Φ29, B103, GA-1, PZA, Φ15, BS32, M2Y, Nf, G1, Cp-1, PRD1, PZE, SF5, Cp-5, Cp-7, PR4, PR5, PR722, L17, ThermoSequenase®, 9° Nm™, Terminator™ DNA polymerase, Tne, Tma, Tfl, Tth, Tli, Stoffel fragment, Vent™ and Deep Vent™ DNA polymerase, KOD DNA polymerase (Sawai, H., et al. 2002. Bioconjugate Chem. 13, 309. Sawai, H., et al. 2001. Chem. Commun. 24, 2604), Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase. Unnatural nucleoside triphosphates can be introduced for example, as described in Malyshev et al., *Nature* 509 (2014): 385-388.

Polymerases from native sources or variants thereof may be screened using an assay that detects incorporation of a non-natural nucleotide having a particular structure. In one example, polymerases can be screened for the ability to incorporate a non-natural nucleotide. Polymerases used herein that can have the ability to incorporate a non-natural nucleotide of a particular structure can also be produced using a directed evolution approach. A nucleic acid synthesis assay can be used to screen for polymerase variants having specificity for a non-natural nucleotide. In some embodiments, such an assay is an in vitro assay, e.g., using a recombinant polymerase variant. Such directed evolution techniques can be used to screen variants of any suitable polymerase for activity toward any of the non-natural nucleotides set forth herein. A polymerase may be used that displays a modified property for the non-natural nucleotide as compared to the wild-type polymerase. For example, the modified property may be, e.g., $K_m$, $k_{cat}$, $V_{max}$, polymerase processivity in the presence of a non-natural nucleotide, average template read-length by the polymerase in the presence of a non-natural nucleotide, specificity of the polymerase for a non-natural nucleotide, rate of binding of a non-natural nucleotide, or any combination thereof. In some embodiments, a polymerase described herein in its wild-type form may be able to incorporate a non-natural nucleotide into an aptamer. In other embodiments, a polymerase described herein may be engineered to incorporate a non-natural nucleotide into an aptamer.

Non-Natural Nucleotides

A non-natural nucleotide may contain a modification to either the base, sugar, or phosphate moiety compared to a naturally occurring nucleotide. A modification may be a chemical modification. Modifications may be, for example, of the 3'OH or 5'OH group of the backbone, of the sugar component, or of the nucleotide base. In some embodiments, the nucleotide is a unnatural nucleoside triphosphate.

In some embodiments, one or more of the 4 naturally-occurring nucleotides (A, G, C, T/U) are replaced with a non-natural nucleotide. In some embodiments, two, three, or all four naturally-occurring nucleotides can be replaced by different non-natural nucleotides.

In some embodiments, a non-natural nucleotide may contain modifications to the nucleotide base. A modified base is a base other than the naturally occurring adenine, guanine, cytosine, thymine, or uracil. Examples of modified bases include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Examples of non-natural nucleotides include, but are not limited to, 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine, 5-methylcytosine (5-me-C), 5-hydroxymethyl cytosine, xanthine, hypoxanthine, 2-aminoadenine, 6-methyl other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyl adenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3', 2': 4,5]pyrrolo[2,3-d]pyrimidin-2-one), 7-deazaadenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, 5-iodouracil, 2-amino-adenine, 6-thio-guanine, 2-thiothymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, and 2-amino-2'-deoxyadenosine. Examples of other synthetic nucleotides may be found in, e.g., Malyshev *Nature.* 509(7500):385, 2014.

In embodiments of the methods and compositions described herein, a non-natural nucleotide comprising a functional group may be incorporated into an aptamer by a polymerase. The ability of a polymerase to incorporate a non-natural nucleotide containing a functional group into an aptamer can in some embodiments enable further modification of the aptamer by a variety of molecules as long as the molecule contains a compatible functional group (also termed herein as a "reactive species") that can react with the functional group in the non-natural nucleotide. Examples of non-natural nucleotides containing a functional group include, but are not limited to, alkyne-modified uridine (1) and aldehyde-modified cytosine (2) as shown in FIG. 12, those described in WO2015021432, and those described in Silverman, *Chem Commun (Camb).* 30:3467-85, 2008.

Functional Groups

In some embodiments, a non-natural nucleotide may have a functional group. The non-natural nucleotide having the functional group may further be modified by reacting with it a binding agent having a compatible functional group. The functional group in the non-natural nucleotide and the compatible functional group in the binding agent react with each other to form a covalent bond, thus, conjugating the binding agent to the non-natural aptamer. Functional groups are specific, chemical reactive moieties within molecules that are responsible for certain chemical reactions, i.e., often chemical reactions with other compatible functional groups. The same functional group may have one or multiple compatible functional groups that it can react with. Compatible functional groups may react with each other to form new bonds and chemical entities. In some embodiments, compatible functional groups may react with each other to form a covalent bond (i.e., covalent conjugation), which may be used to link to molecules together. In some embodiments, a non-natural nucleotide containing a functional group may be used to conjugate an amino acid, a small molecule (e.g., a sugar molecule), a peptide (e.g., a synthetic peptide), a protein (e.g., a synthetic protein), or a non-biological moiety to the aptamer.

As described herein, a binding agent and a non-natural aptamer may be covalently conjugated to each other by reacting their respective functional groups in a covalent conjugation reaction. Compatible functional groups that may react with each other to form a covalent bond are well-known in the art. Examples of compatible functional groups include, but are not limited to, e.g., terminal alkyne and azide, maleimide and cysteine, amine and activated carboxylic acid, thiol and maleimide, activated sulfonic acid and amine, isocyanate and amine, azide and alkyne, and alkene and tetrazine.

For example, if one of the functional groups is an amino group, examples of functional groups capable of reacting with amino groups include, e.g., alkylating and acylating agents. Representative alkylating agents include: (i) an α-haloacetyl group, e.g., XCH2CO— (where X=Br, Cl, or I); (ii) a N-maleimide group, which may react with amino groups either through a Michael type reaction or through acylation by addition to the ring carbonyl group; (iii) an aryl halide, e.g., a nitrohaloaromatic group; (iv) an alkyl halide; (v) an aldehyde or ketone capable of Schiff's base formation with amino groups; (vi) an epoxide, e.g., an epichlorohydrin and a bisoxirane, which may react with amino, sulfhydryl, or phenolic hydroxyl groups; (vii) a chlorine-containing of s-triazine, which is reactive towards nucleophiles such as amino, sufhydryl, and hydroxyl groups; (viii) an aziridine, which is reactive towards nucleophiles such as amino groups by ring opening; (ix) a squaric acid diethyl ester; and (x) an α-haloalkyl ether. Examples of amino-reactive acylating groups include, e.g., (i) an isocyanate and an isothiocyanate; (ii) a sulfonyl chloride; (iii) an acid halide; (iv) an active ester, e.g., a nitrophenylester or N-hydroxysuccinimidyl ester; (v) an acid anhydride, e.g., a mixed, symmetrical, or N-carboxyanhydride; (vi) an acylazide; and (vii) an imidoester. Aldehydes and ketones may be reacted with amines to form Schiff's bases, which may be stabilized through reductive amination.

It will be appreciated that certain functional groups may be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

IV. Cu-Catalyzed Azide-Alkyne Cycloaddition (CuAAC)

In some embodiments of the methods and compositions described herein, a non-natural nucleotide in a non-natural aptamer may contain an alkyne or azide functional group. Two functional groups, a terminal alkyne and an azide, may undergo copper(I)-catalyzed azide-alkyne cycloaddition (CuAAC; also referred to as Cu-catalyzed click chemistry or simply click chemistry) to form the covalent moiety 1,2,3-triazole. In some embodiments, a non-natural aptamer with a non-natural nucleotide having an alkyne functional group may be further modified with a binding agent having an azide functional group. In other embodiments, a non-natural aptamer with a non-natural nucleotide having an azide functional group may be further modified with a binding agent having an alkyne functional group.

While the reaction CuAAC can be performed using commercial sources of copper(I) such as cuprous bromide or iodide, the reaction works much better using a mixture of copper(II) (e.g., copper(II) sulfate) and a reducing agent (e.g., sodium ascorbate) to produce Cu(I) in situ. As Cu(I) is unstable in aqueous solvents, stabilizing ligands (e.g., TBTA (tris-(benzyltriazolylmethyl)amine), THPTA (tris(hydroxypropyltriazlylmethyl) amine), BTTES (bis[(tert-butyltriazoyl)methyl]-[(sulfoxy ethyltriazoyl)methyl]-amine), BTTAA (bis[(tert-butyltriazoyl)methyl]-[2-carboxymethyltriazoyl) methyl]-amine) are effective for improving the reaction outcome. The reaction can be run in a variety of solvents, and mixtures of water and a variety of miscible organic solvents including alcohols, DMSO, DMF, tBuOH, and acetone. In particular embodiments, the reaction condition includes $CuSO_4$, THPTA ligand, and sodium ascorbate in water.

As described herein, in particular embodiments, a polymerase may incorporate a non-natural nucleotide containing a terminal alkyne into an aptamer, thus creating a non-natural aptamer containing a terminal alkyne functional group. The terminal alkyne-containing non-natural aptamer may be further labeled with any molecule containing an azide as the compatible functional group. For example, C8-alkyne-deoxyuridine is well tolerated by commercially-available polymerases, and enables chemical modification of an aptamer through CuAAC without polymerase engineering. As described herein, non-natural aptamers containing C8-alkyne-deoxyuridine may react with azide-containing binding agents in Cu-catalyzed click chemistry directly on the sequencer flow cell. In other embodiments, a polymerase may incorporate a non-natural nucleotide containing an azide into an aptamer, thus creating a non-natural aptamer containing an azide functional group. The azide-containing non-natural aptamer may be further labeled with any molecule containing a terminal alkyne as the compatible functional group.

V. Cu-Free Azide-Alkyne Cycloaddition

In some embodiments of the methods and compositions described herein, an alkyne and an azide may undergo copper-free azide-alkyne cycloaddition (also referred to as Cu-free click chemistry) to form the covalent moiety 1,2,3-triazole. Copper-free azide-alkyne cycloaddition makes use of alkynes activated by ring strain, such as cyclooctynes, to accelerate the triazole-forming reaction. Such strain-promoted cycloadditions, even without catalysts such as Cu(I), can proceed efficiently. Examples of cyclooctynes are available in the art and include, but are not limited to, monofluorinated cyclooctynes, difluorinated cyclooctynes, and aryl cyclooctynes (e.g., dibenzocyclooctyne and biarylazacyclooctynone). Examples of cyclooctynes that may be used in copper-free azide-alkyne cycloaddition are described in, e.g., Sletten and Bertozzi, *Acc Chem Res.* 44(9):666, 2011, Baskin et al., *Proc Natl Acad Sci USA* 104(43):16793, 2007, Yao et al., *J Am Chem Soc.* 134(8):3720, 2012, and Kuzmin et al., *Bioconjug Chem.* 21(11):2076, 2010.

In some embodiments, a non-natural aptamer with a non-natural nucleotide having a cyclooctyne functional group may be further modified with a binding agent having an azide functional group. In other embodiments, a non-natural aptamer with a non-natural nucleotide having an azide functional group may be further modified with a binding agent having a cyclooctyne functional group.

As described herein, in particular embodiments, a polymerase may incorporate a non-natural nucleotide containing a cyclooctyne into an aptamer, thus creating a non-natural aptamer containing a cyclooctyne functional group. The cyclooctyne-containing non-natural aptamer may be further labeled with any molecule containing an azide as the compatible functional group. As described herein, non-natural aptamers containing one or more cyclooctynes may react with azide-containing binding agents in copper-free azide-alkyne cycloaddition directly on the sequencer flow cell. In other embodiments, a polymerase may incorporate a non-natural nucleotide containing an azide into an aptamer, thus creating a non-natural aptamer containing an azide functional group. The azide-containing non-natural aptamer may be further labeled with any molecule containing a cyclooctyne as the compatible functional group.

VI. Solid Support

In methods and compositions described herein, a solid support may be a material to which aptamers or complements thereof can be attached and is amenable to at least one detection method. Possible solid supports include, but are not limited to, a polystyrene surface, a polypropylene surface, a gold surface, a glass surface, or a silicon wafer. Other possible materials for a solid support may be, e.g., glass and modified or functionalized glass, plastics (including acrylics, polystyrene and copolymers of styrene and other materials, polypropylene, polyethylene, polybutylene, polyurethanes, TEFLON®, and the like), nylon or nitrocellulose, resins, silica or silica-based materials including silicon and modified silicon, carbon, metals, inorganic glass, plastics, optical fiber bundles, and a variety of other polymers.

Solid supports used in methods and compositions of the disclosure may be fashioned into a variety of shapes. In certain embodiments, the solid support may be substantially planar, such as plates (e.g., slides), microtiter plates, flow cells, coverslips, microchips, and the like. The surface of the solid support may be further modified to contain tiles, wells, trenches, grooves, depressions, or the like. In further embodiments, microspheres or beads may be placed in the wells, i.e., through covalent conjugation. Further, the solid support may be modified to contain chemical functional groups, e.g., amino groups, carboxy groups, oxo groups, thiol groups, and the like. The chemical functional groups may be used to conjugate short polynucleotides that are complementary to the adaptors at the ends of aptamers or complements thereof. To perform bridge amplification in methods described herein, the aptamers or complements thereof may comprise a first adaptor at a first end and a second adaptor at a second end. The aptamers or complements thereof containing the adaptors may be hybridized to a solid support containing short polynucleotides that are complementary to the adaptors linked to its surface. The solid support surface may be linked to a plurality of sequence-identical short polynucleotides that are complementary to the first adaptor in the aptamer or complement thereof, and a plurality of sequence-identical short polynucleotides that are complementary to the second adaptor in the aptamer or complement thereof.

In particular embodiments, a solid support used in methods and compositions of the disclosure may be a flow cell. A flow cell may include a flow cell body having a channel that is configured to convey a solution through the flow cell body. A flow cell may also include a bottom surface and a top surface. The top surface may be transparent to permit light to pass through. The flow cell body may include fluidic inlet and outlet ports that are in fluid communication with the channel. A pump cavity may also be provided in the flow cell body. The pump cavity may communicate with and be interposed between an end of the channel and one of the fluidic inlet and outlet ports. An electroosmotic (EO) pump may be placed in the pump cavity. The EO pump induces flow of the solution through the EO pump and channel between the fluidic inlet and outlet ports.

A solid support may be a patterned flow cell. A patterned flow cell may use distinct nanowells for cluster generation to make more efficient use of the flow cell surface area. This flow cell design contributes to increased data output, reduced costs, and faster run times. In some embodiments, a patterned flow cell may contain millions to billions of nanowells at fixed locations across the surface of the flow cell. The structured organization provides even spacing of sequencing clusters that is advantageous over non-patterned cluster generation. Precise nanowell positioning eliminates the need to map cluster sites and saves time on each sequencing run. Clusters formed in the nanowells further make the flow cells less susceptible to overloading and more tolerant to a broader range of library densities.

VII. Systems

Also provided are systems for implementing the sequencing and binding assay described herein. Exemplary systems can include, for example, a flow cell or other support on which the solid support linked to the aptamers can reside, a detector to detect signal in clusters from sequencing of the aptamers and for detecting signal from target molecule binding to aptamers in a cluster. The detector can be for example a confocal scanner, confocal microscope, or CCD-based system. An exemplary detection system for fluorescent labels is a charge-coupled device (CCD) camera, which can optionally be coupled to a magnifying device, for example a microscope. Using such technology it is possible to simultaneously monitor many colonies in parallel.

In some embodiments, the systems include a non-transitory computer readable medium coupled to a processor. In some embodiments, the non-transitory computer readable medium comprises code executable by the processor for performing a method comprising one or more of the following steps: recording nucleotide sequences and locations of aptamers in the clusters; recording signal from target molecule binding to aptamers in the clusters; correlating target molecule binding signal and sequence with common locations; and outputting sequences of aptamers that bind to the target molecule.

The system may automatically perform all steps required for non-natural aptamer discovery, including sequencing, click-chemistry, and affinity measurement steps. First, the system may generate a single read of each sequence for the entire aptamer library through standard sequencing (e.g., Illumina sequencing). At this point, the sequencer flow cell may be coated with sequence-identified clusters of unmodified, anti-sense, single-stranded DNA oligonucleotides. Next, the system may incorporate non-natural nucleotides during the synthesis step for the second read, replacing a natural nucleotide (e.g., A, T, G, or C) with a modified nucleotide. These bases create the foundation for the addition of flexible modifications through modification with a reactive species (e.g., which can include but is not limited to copper (Cu)-catalyzed click chemistry) directly on the sequencer flow cell, forming non-natural aptamer clusters. Third, the system may perform a fluorescence-based binding assay to measure the binding affinity of every non-natural aptamer on the flow cell. In some embodiments, this binding assay may employ the sequencer's built-in epifluorescence microscope and image analysis software. A software package may also be used to extract and analyze the output of the binding assay, matching each aptamer sequence with its measured binding affinity.

VIII. A Machine Learning (ML) Algorithm for Computationally-Directed Evolution The theoretical sequence space available to aptamers ($\sim 4^{45}$) is far larger than the number of sequences that can realistically be explored in a single screening method as described herein (e.g., $10^6 \sim 10^7$). A data-efficient machine learning (ML) algorithm that can identify critical motifs (k-mers) can be used to predict new aptamers with potentially superior binding performance thereby selecting aptamers sequences enriched algorithmically for the ability to bind a particular target. Once aptamer sequences are identified, all or a subset of these aptamers may be synthesized using commercial pooled synthesis approaches (e.g., available for example from Twist Bioscience, San Francisco, CA). The pool of aptamers may be further evolved through subsequent screening. This combination of massively parallel, sequence-linked binding measurements with ML-based predictions provides the ability to identify superior aptamers by exploring sequence space that is currently inaccessible to traditional in vitro directed evolution methods due to the number of potential library members. An integrated platform that greatly streamlines and accelerates the discovery of non-natural aptamers for a wide range of targets in complex media may be produced. The instrument may be based on a commercially available sequencer with a small, benchtop footprint.

Figure 10:
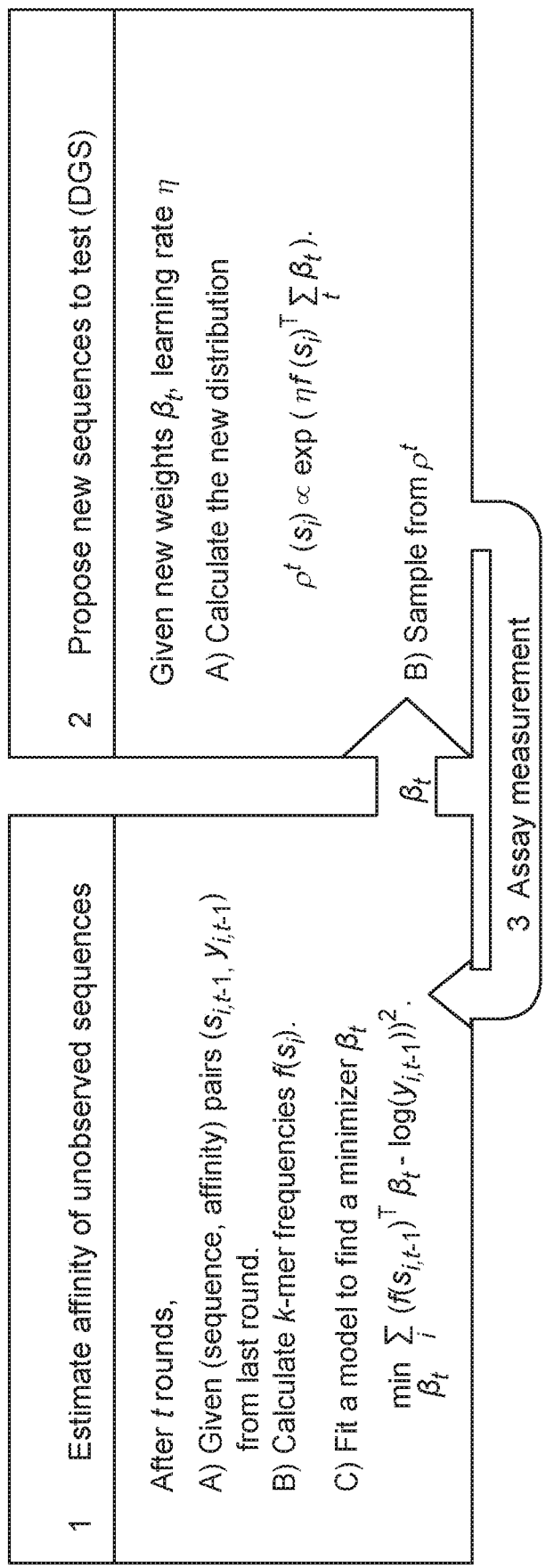
FIG. 10: Computational aptamer design cycle. This procedure consists of affinity estimation via log-linear modeling (step 1) and sequence design via exponential sampling (step 2). Affinity estimation finds a minimum square error estimator under a model that posits that the log affinity of any aptamer can be decomposed into the sum of log-affinities of short (8-10 base long) DNA k-mers. Sequence design with the DeBrujin graph sampling (DGS) approach proceeds by maintaining an in silico population ($p^t$) over all possible ($4^{45}$) aptamer sequences. Given a new affinity model ($\beta^t$), the population was updated by exponentially up-weighting aptamers predicted to have high affinity. Finally, DGS efficiently samples the in silico population to propose the next N2A2 experiment (step 3).

A robust, log-linear motif-based model for identifying key sequences that determine aptamer binding affinity can be used. Specifically, in some embodiments, the model combines the contribution of short DNA k-mers appearing in the aptamer in a log-linear way, which forms an accurate, robust model with relatively few parameters (FIG. 10, step 1). This k-mer-based approach has been extremely successful in analyzing genomic DNA data [42] and makes use of recent advances in fitting short DNA sequence-based models [43]. Using this log-linear motif model, a provably optimal technique for in silico aptamer evolution, DeBruijn graph sampling (DGS), can be used. The DGS algorithm balances two conflicting goals: exploring entirely new sequences, and improving existing sequences. This may be accomplished by keeping track of an in silico aptamer population across experiments, exponentially down-weighting any aptamers predicted to have low binding affinity by the model, and sampling from the aptamer population to generate a new experiment (FIG. 10, step 2). By precisely controlling how sequences are down-weighted, the exploration vs improvement tradeoff can be balanced.

The DGS approach can exactly store, down-weight, and sample the population of aptamers (e.g., $4^{45}$ aptamers) using a compressed, k-mer-based representation of the aptamer called the DeBruijn graph. First, if the data follows the log-linear motif model, then DGS corresponds to performing idealized SELEX, where the population of aptamers in each round evolves according to ideal selection over all possible ($4^{45}$) aptamer sequences using an infinite number of molecules. Second, even if the data does not follow a log-linear motif model, the DGS procedure will improve the average binding affinity over the aptamer population. In fact, DGS corresponds to a type of gradient descent over the space of aptamer populations.

A potential problem is insufficient predictive power of the log-linear model for the data generated from the solid support clusters as described herien, either due to inherent stochasticity in the measurement system or strong nonlinearities in the binding affinity measurement system. In this case, three potential alternatives to the affinity prediction model may be tested. The first is convolutional neural networks over the sequences, which have recently proven to be competitive with log-linear k-mer models in genomic DNA sequence prediction tasks [45]. Second, higher-order k-mer models may be tested, where interaction terms between the k-mer sequences may be included [46]. Finally, ensembles over the proposed models could combine the strengths of the above models. These changes make step 2 of the analysis (FIG. 10, right) more computationally challenging, however, as the sampling over the in silico aptamer population would no longer be exact. In some embodiments, one can use Gibbs sampling, with the current sampling scheme as an initial approximation. In addition, in some embodiments, one can generalize the model to handle arbitrary monotonic transformations over the response variable, substantially expanding the applicability of the model. In this case, the schematic in FIG. 10 will change such that we would replace equation 3 in Step 1 with what is known as a single-index model estimate. In some embodiments, as a first step, one can apply the isotron estimator (A. T. Kalai and R. Sastry, "The Isotron Algorithm: High-Dimensional Isotonic Regression," in COLT, 2009) as a way to derive model estimate ($\beta$).

Accordingly, methods and systems for performing the method are provided for using machine learning to improve and optimize aptamer libraries for binding to a target molecule. For example, in some embodiments, the methods comprise generating a data set representing binding data of a target molecule to an initial library of aptamers, generating a machine learning model using the data set as a training data set, generating with the machine learning model a new untested library of aptamers predicted to have desired binding properties for the target molecule, and testing the new untested library of aptamers for binding to the target molecule. Generating a data set representing binding data of a target molecule to an initial library of aptamers can include receiving the data set or physically testing the binding of the target molecule to the aptamers and recording the binding affinity for the aptamers along with their sequence. Generating a new untested library of aptamers predicted to have desired binding properties for the target molecule with the machine learning model can include generation of new untested aptamer sequences based on subsequences of aptamers having known binding affinities or by inputting new untested aptamer sequences as test data and receiving predicted target molecule binding affinity for the new untested aptamer sequences.

Different machine learning techniques—including but not limited to linear support vector machine (linear SVM), boosting for other algorithms (e.g., AdaBoost), neural networks, logistic regression, naive Bayes, memory-based learning, random forests, bagged trees, decision trees, boosted trees, or boosted stumps—may be used in different embodiments.

The above-described method steps of providing binding data for aptamers, training a machine learning model, outputting new untested aptamer sequences predicted to have a target molecule binding affinity, and then testing those new aptamer sequences can be repeated multiple (e.g., 2, 3, 4, 5, or more) times to provide a further improved plurality of aptamers sequences for binding to a target molecule.

The new untested library of aptamers can be generated as desired. In some embodiments, methods of oligonucleotide synthesis as described in any of US Patent Publication Nos. 20180104664; 20180029001; or 20160303535 can be used to generate the new untested library. The aptamer libraries can optionally be modified to include the at least one non-natural nucleotide as described herein and can optionally be modified to be covalently linked to a binding agent as described here.

In some embodiments, generating the machine learning model comprises calculating or predicting affinity (e.g., log affinity) of aptamer binding as a function of aptamer subsequence affinities. For example, the function can be a sum of log-affinities of subsequence k-mers. Subsequence length can be determined as desired. In some embodiments, the subsequences are 6-12 bases or 8-10 bases long. In some embodiments, DeBruijn graph sampling is employed.

Figure 17:
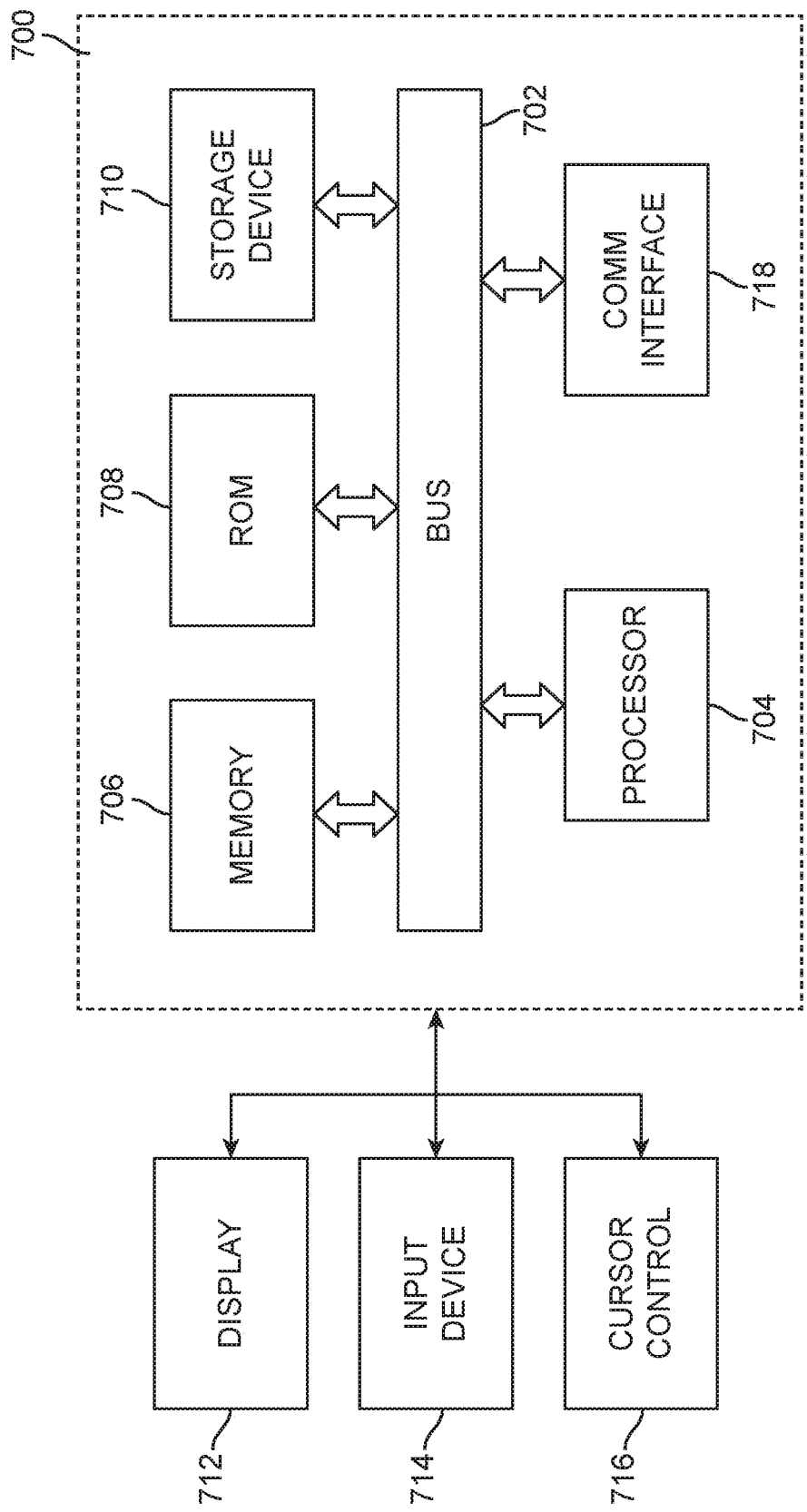
FIG. 17 is a block diagram of a computer system in accordance with an embodiment.

FIG. 17 shows a block diagram of an example computer system 700 usable with system and methods according to embodiments of the present invention. The computer system 700 can be used to run the program code for various method claims according to embodiments of the present invention.

Any of the computer systems mentioned herein may utilize any suitable number of subsystems. Examples of such subsystems are shown in FIG. 17 in computer apparatus 700. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 17 are interconnected via a system bus 775. Additional subsystems such as a printer 774, keyboard 778, fixed disk 779, monitor 776, which is coupled to display adapter 782, and others are shown. Peripherals and input/output (I/O) devices, which couple to I/O controller 771, can be connected to the computer system by any number of means known in the art, such as serial port 777. For example, serial port 777 or external interface 781 can be used to connect computer system 700 to a wide area network such as the Internet, a mouse input device, or a scanner. The interconnection via system bus 775 allows the central processor 773 to communicate with each subsystem and to control the execution of instructions from system memory 772 or the fixed disk 779, as well as the exchange of information between subsystems. The system memory 772 and/or the fixed disk 779 may embody a computer readable medium. Any of the values mentioned herein can be output from one component to another component and can be output to the user.

A computer system can include a plurality of the same components or subsystems, e.g., connected together by external interface 781 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure (e.g., the machine learning aspects) can be implemented in the form of control logic using hardware and/or using computer software in a modular or integrated manner.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

EXAMPLES

Example 1—Non-Natural Aptamer Synthesis

Conversion of DNA clusters into non-natural aptamer clusters (steps 1 and 2): A natural DNA library containing an N40 random region flanked by primer binding sites was sequenced on a MiSeq as single-end reads. The sequencer chemistry code was modified to test a wide range of commercially available family B polymerases that are known to tolerate replacement of natural dTTP with C8-Ak-dUTP. KOD-XL polymerase was most effective at incorporating the modified nucleotides through bridge PCR amplification, and successfully converted DNA clusters into non-natural aptamers containing C8-alkyne-dUTP (FIG. 3A).

EcoR1 cleavage of primers (step 3): An EcoR1 cleavage site was incorporated between the primer and the binding region of each sequence in the aptamer library. After the non-natural clusters were formed, EcoR1 enzyme and a DNA strand complementary to the EcoR1 site were added. This resulted in site-specific cleavage of the primer sequences. The sequencing polymerase used by Illumina sequencing will only incorporate a template-free dATP onto the 3' end of unprotected sequences on the flow cell. Since sequences that have not been cut remain protected, only those that were successfully cleaved will have the fluorescently-labeled dATP added. After EcoR1 treatment, all clusters containing the restriction site had been labeled with fluorescent dATP, confirming successful primer removal.

Click chemistry using CuAAC (Step 4): Several CuAAC conditions (solvents, chelators, temperature, time, etc.) were tested on flow cells using a fluorescent microscope and azide-labeled fluorophores to assess the stability of the flow cells under different reaction conditions. CuSO4/Tris(3-hydroxypropyltriazolylmethyl)amine (THPTA) and sodium ascorbate in water were found to produce the highest yields (~100%) in 20 minutes, with little to no damage to the flow cell surface. Therefore, these conditions were chosen for proof of concept on the Non-Natural Aptamer Array (N2A2) system. An azido-modified fluorophore was conjugated onto the clusters at C8-alkyne-dUTP bases using these CuAAC conditions, and dUTP modification was imaged successfully (FIG. 3B).

Example 2—Sequencing and Screening Binding Performance of Aptamers

Figure 5A:
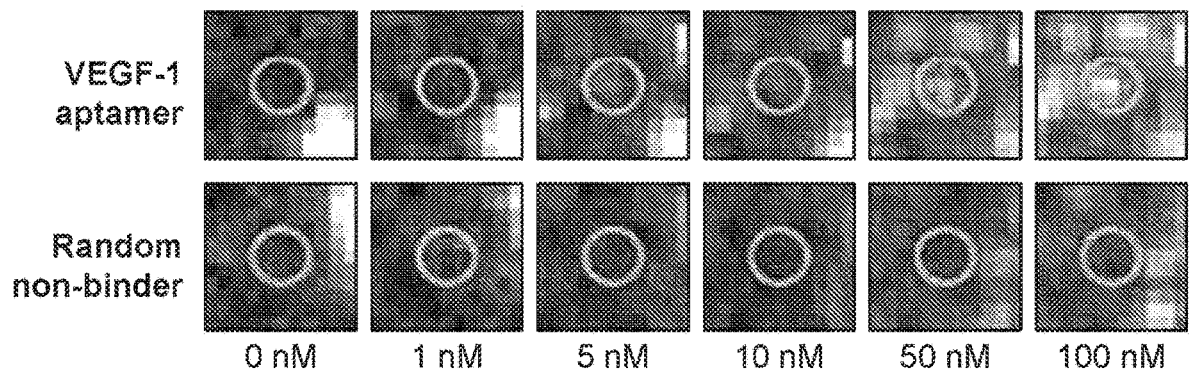
FIGS. 5A and 5B: Mock selection of VEGF aptamers.

To test the ability to both sequence and screen binding performance of aptamers on the N2A2 system, a "mock selection" for the vascular endothelial growth factor (VEGF) protein was performed by spiking previously reported VEGF aptamers into a random library. To assess the system's ability to differentiate between aptamers with different target affinities, a 26-nt aptamer (VEGF-1) [27] with a dissociation constant (Kd) of 0.5 nM, and a 66-nt aptamer (VEGF-2) [28] with Kd=120 nM were tested. These two sequences were spiked into a random library and standard MiSeq cluster generation and sequencing of each cluster were performed on the flow cell, verifying that both aptamers were present in the pool. The flow cell was then exposed to a titration series of fluorescently-labeled VEGF to evaluate each cluster's binding performance. Individual cluster images show that the intensity of clusters containing a known VEGF aptamer sequence increased as the target concentration increased, indicating binding (FIG. 5A, top), while no such increase was seen for the random library clusters, confirming that nonspecific target binding is not a problem (FIG. 5A, bottom).

Figure 5B:
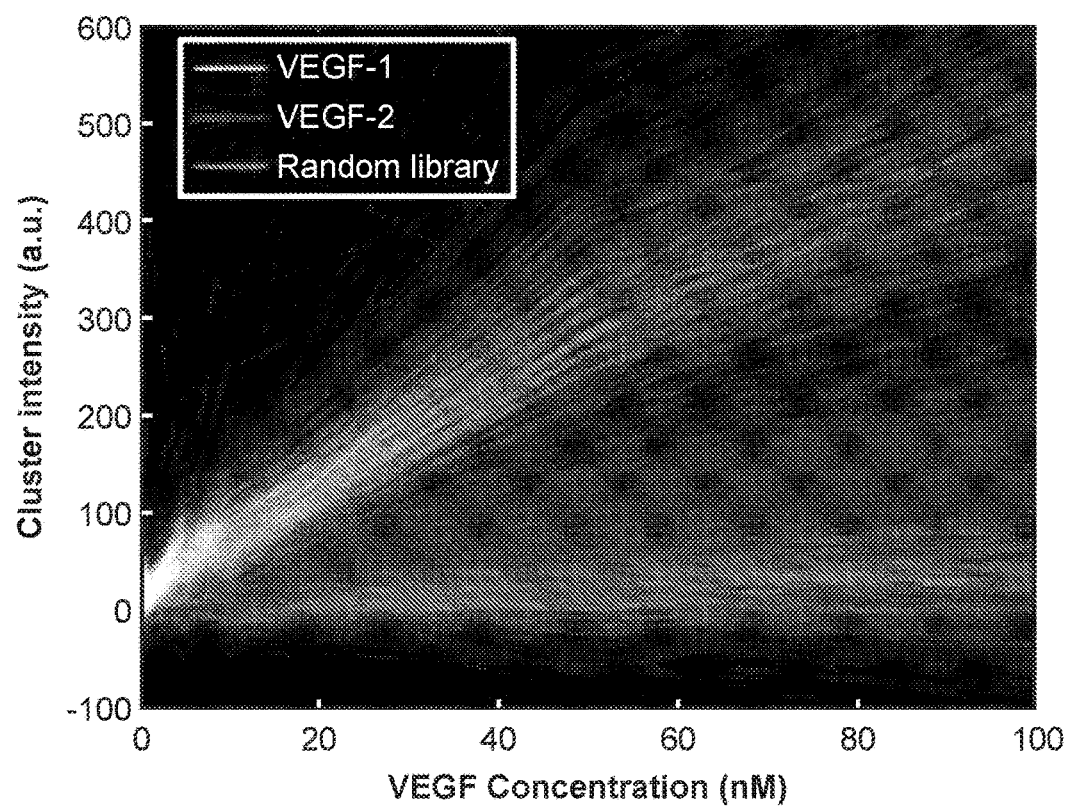

Having verified target binding by examining single cluster intensities, the MiSeq's powerful built-in image analysis capabilities was used to evaluate the intensities of millions of clusters simultaneously. Discernible differences were observed in binding behavior between the two aptamers and the random library, even when analyzing thousands of clusters across the flow cell (FIG. 5B). Although there is some spread in the observed intensity values for different clusters containing the same sequence due to variations in cluster density, flow cell location, and image analysis noise, the two VEGF aptamers show Langmuir-like binding behavior, and the observed superior affinity of VEGF-1 relative to VEGF-2 reflects their reported binding affinities. Importantly, this measured binding data with known aptamers allowed the characterization of the method's ability to discriminate clusters that bind a target from clusters that do not—a critical ability in discovering new aptamers for new targets.

Example 3—Tyrosine-Modified Non-Natural Aptamers

A de novo screen for non-natural aptamers for programmed cell death protein 1 (PD-1) is performed by utilizing the polymerase and click chemistry methods described herein to incorporate a tyrosine (Tyr) modification into the pre-enriched library. Tyr was chosen due to its high abundance on the binding interface between PD-1 and its natural ligand PD-L1. Three rounds of pre-enrichment with the aptamer library and target immobilized on beads are performed, which allow for the library to be reduced from $10^{15}$ sequences to a scale that can be easily represented on a flow cell (~$10^8$ sequences). The random DNA is be incubated for 45 mins with PD-1 attached to magnetic beads. The beads are then be washed three times to remove any unbound DNA from the beads. The beads are then heated to elute any library members that bind PD-1. The eluted sequences are then PCR amplified for the next round.

This pre-enriched library is sequenced and incubated with increasing concentrations (500 pM to 100 nM) of fluorescently-labelled PD-1. Each concentration is be incubated within the flow cell for 45 minutes at 22° C. in binding buffer (1×SSC, 1 mM $MgCl_2$, 1 mM $CaCl_2$), 5 mM KCl, 0.05% Tween20). Following each incubation, the flow cell is imaged and then stripped of labeled protein using 0.05 N NaOH and 0.25% SDS before beginning the next incubation. Single rounds of both natural and Tyr-modified selections are carried out for PD-1, providing a direct head-to-head comparison of the two libraries. This demonstrates the power of adding greater functionality to the DNA bases.

Using the algorithm described herein, the top 6,000 binders for PD-1 are identified. Then, utilizing Twist Biosciences' pooled oligonucleotide synthesis platform, the top 6,000 sequences from the experiment are chosen and synthesized as a pool. This pool is then placed back into the N2A2, thereby allowing for hundreds of replicate binding curves for each sequence. This provides the ability to gain statistical information about all 6,000 sequences, ensuring that the very best sequence for the downstream application is chosen. In order to verify the accuracy of the binding measurement on the N2A2, the top 10 sequences are synthesized and further characterized using two different measurement techniques (fluorescence and microscale thermophoresis).

Potential challenges may include the length of the linker on the modified bases, and the modification itself. If the initial selections do not yield high quality aptamers, several alternative modified bases with a variety of linkers may be explored to determine the ideal combination for the majority of selections. Previous work has established that the majority of protein targets may bind to aptamers modified with Tyr, Trp, or Phe. Tyr may typically be used at first as the modification of choice for large protein targets, as it is commonly abundant at the binding interface of proteins. However, other modifications may be explored should the initial Tyr modification not yield functional aptamers. This system may be utilized for selections against a wide array of targets, and the information gained regarding the optimal combination for this PD-1 selection may guide the choices of modified bases and linkers for future selections.

Example 4—Identifying Aptamer Candidates from a Large Random Pool

To identify aptamer candidates from a large random pool, a statistical classifier that identifies aptamer candidates based on their cluster intensities during target binding was developed. This classifier uses the measured binding intensities at various target concentrations to detect clusters that represent genuine binding sequences while rejecting false-positive signals arising from image analysis noise and nonspecific binding. The output of the classifier is the top 6,000 binding candidates out of a pool of ~15 million sequences. To characterize the classifier's sensitivity for discovering true binders in a low-abundance pool, an in silico experiment was performed in which the addition of varying copy numbers of the VEGF-1 aptamer into a random library was simulated. It was found that the classifier could reliably detect as few as 2 individual VEGF clusters out of 14 million random sequences. N2A2 screening was carried out as described above.

Figure 6:
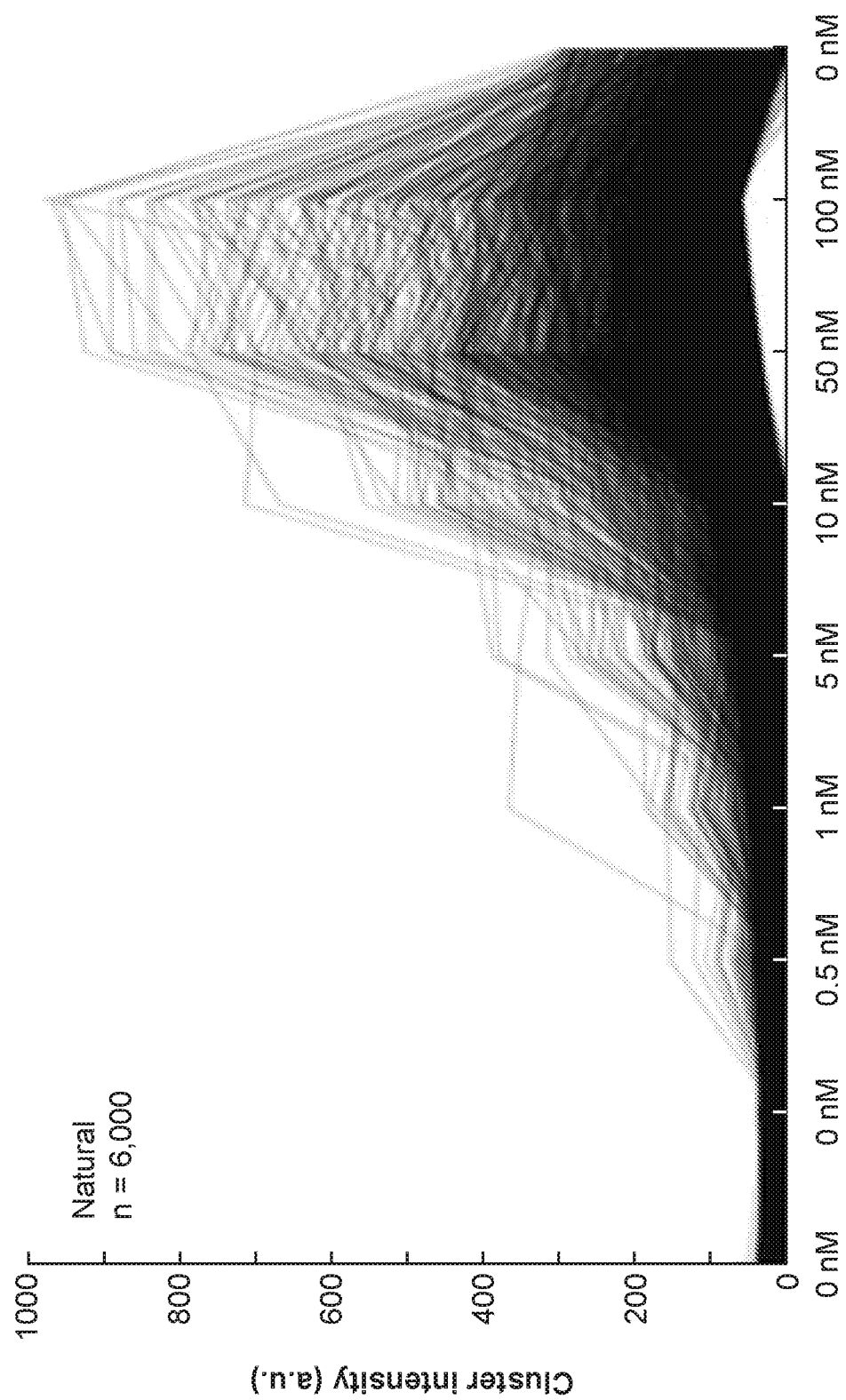
FIG. 6: Natural DNA aptamer candidates identified for PD-1 after a single round of N2A2 analysis. Each line represents a single cluster with a unique sequence.

A single round of selection on a natural DNA library for PD-1 was subsequently performed. As FIG. 6 demonstrates, ~6,000 unique sequences out of 10 million that exceed the threshold for binding were identified. These sequences may be synthesized and subjected to a second round of N2A2 analysis before beginning ML selections.

Example 5—DeBrujin Graph Sampling (DGS) Model Prediction

Figure 11:
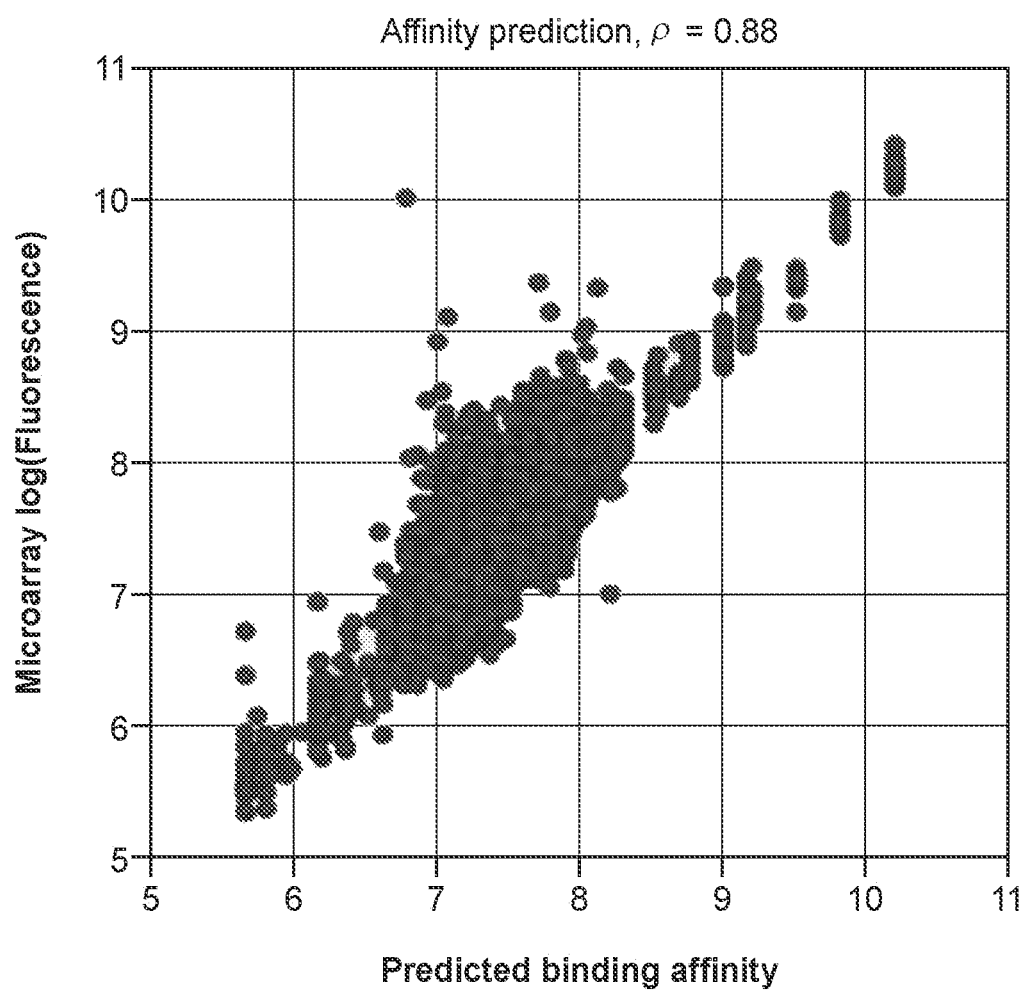
FIG. 11: Log linear k-mer-based models accurately predict the binding affinity of un-observed sequences.

A prediction experiment based upon prior DNA aptamer assays was conducted in which 82,081 45-base sequences derived from a SELEX-style assay against thrombin [4] were synthesized. Their binding affinity was measured using microarray fluorescence. The model was then fitted on half of this data, and the performance of the k-mer model on the remaining half of the aptamers was evaluated. FIG. 11 shows that the k-mer model has high concordance with observed microarray data, with a Pearson correlation of 0.88. These sequences were never observed, and yet the model can clearly identify the highest-affinity sequences. The model additionally identifies the well-known Bock aptamer as the highest binding affinity sequence, despite never observing sequences similar to this aptamer.

A simulation experiment was used to test whether DGS could have discovered the best thrombin binding sequences with fewer measurements. Using the microarray data above, a thrombin binding simulator which replicates the measured aptamer binding affinities and adds noise that matches replicate variances from the original assay was constructed. The best aptamer was consistently found in less than 5,000 binding affinity measurements where prior computational design approaches such as in-silico mutagenesis and selection fail completely.

Example 6—Experimental Procedures for Natural and Non-Natural VEGF Aptamer Measurements on N2A2

To show the power of N2A2 to perform deep analysis and discovery in DNA aptamer pools with natural and modified base chemistries, we sequenced and performed binding assays for a large library (~10^6 unique sequences) of aptamers targeting the protein VEGF, using both natural DNA and non-natural DNA with two different base modifications. Our results show that N2A2 can discover high performing aptamers that would never be discovered through the traditional aptamer selection workflow.

Natural Aptamer Pool Generation

Starting with a random DNA library, we generated a pool of aptamers targeted against VEGF through a combination of traditional aptamer selection methods (SELEX) and our lab's previously demonstrated aptamer screening technique, particle display (PD) (Wang et al., Angew. Chemie, 126:1, 2014). Briefly, one round of traditional SELEX was performed to reduce the starting DNA library diversity and enrich sequences with higher affinity to VEGF. We then performed 5 rounds of particle display screening on this pre-enriched aptamer pool, in each round selecting and amplifying the sequences that displayed the highest binding affinity to VEGF as indicated by a fluorescence flow cytometry assay. This iterative process is designed to enrich the aptamer sequences that bind to VEGF with the highest affinity. The pools of DNA sequences at the end of each round (named "R0" after the initial round of SELEX, and "R1" through "R5" after each round of particle display) were subsequently prepared for high-throughput sequencing and binding analysis on the N2A2 via attachment of Illumina sequencing adapters.

N2A2 Setup for VEGF Binding Assays

We used N2A2 to measure the VEGF binding affinity of all sequences in these pools simultaneously. We performed three separate experiments: 1) VEGF binding to the natural DNA pools, 2) VEGF binding to non-natural DNA modified with tryptophan, and 3) VEGF binding to non-natural DNA modified with tyrosine. In addition to the six aptamer pools described above (R0-R5), we included three other DNA sequences on the flow cell for each experiment: (1) a known "fiducial mark" sequence with a fluorescently-labeled complement for intensity calibration, (2) a "positive control" sequence based on a published aptamer known to bind to VEGF, and (3) a "negative control" sequence known not to bind to VEGF. The same input DNA stocks and labeled VEGF protein were used for all three experiments, but new sequencing cartridges and flow cells were used for each separate experiment. Other details of experimental setup of the sequencing cartridge, protein titrations, and software and hardware modifications have previously been described in the provided grant document and manuscript. VEGF protein was labeled with Dylight647 fluorophore to enable imaging on the N2A2.

N2A2 Analysis of Natural DNA Aptamers for VEGF

Figure 13:
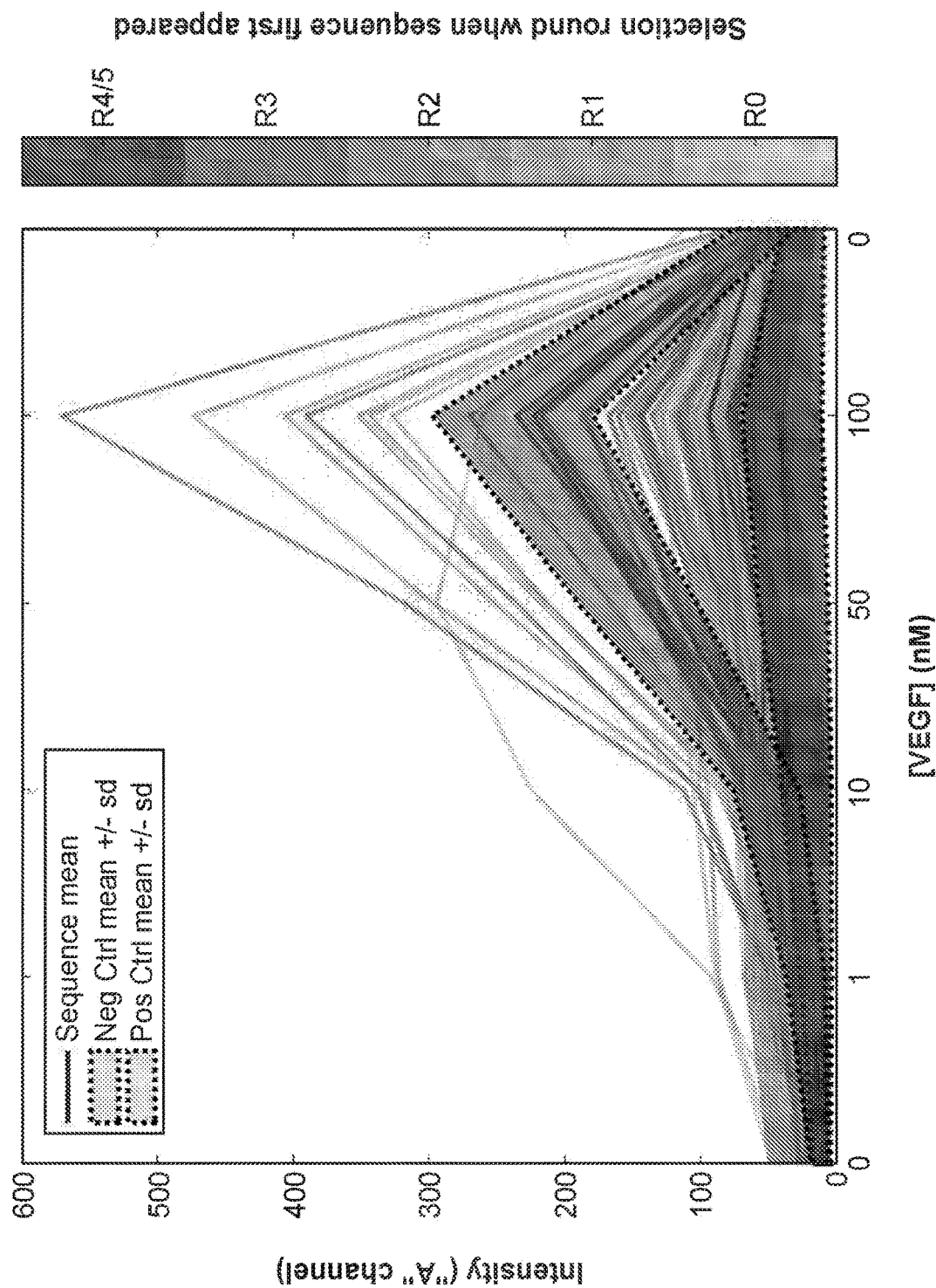
FIG. 13: Binding analysis of natural DNA aptamer pools to VEGF.

Using the N2A2, we exposed the natural DNA aptamer libraries to VEGF concentrations ranging from 10 pM to 100 nM VEGF. To analyze binding across all sequences while minimizing the effect of measurement noise, we used the following workflow. First, we identified the copy number for each sequence on the flow cell (that is, for a given sequence, how many individual replicates or "reads" of that sequence were present on the flow cell). Second, we restricted our analysis only to those sequences with at least 60 copies on the flow cell (at least 10 copies in each pool from R0 to R5) to ensure sufficient replicates and minimize noise. Third, for each of these sequences, we averaged the fluorescence intensity of all clusters with that sequence at each VEGF concentration tested, such that we can report a single averaged fluorescence for each individual sequence. We then plotted these averaged fluorescence measurements for each sequence as a function of VEGF concentration (FIG. 13). Each sequence's binding curve is color-coded by the round of selection in which that sequence first appeared. To give a sense of background binding as well as the typical variability in intensity data for "dark" clusters with the same sequence, the binding of the negative control sequence is plotted as the grey shaded region, which covers the mean intensity+/−one standard deviation across all clusters with this sequence. To show the magnitude and variability of a "true" binding sequence, we plotted the data for all clusters matching the positive control sequence as the red shaded region, which covers the mean intensity+/−one standard deviation across all clusters with this sequence.

The analysis of all natural DNA sequences in FIG. 13 shows several interesting features. First, a range of apparent binding affinities is observed, with many sequences appearing to bind above background intensities but below the positive control intensity, some sequences binding with roughly the same intensity as the positive control, and a handful of sequences showing significantly higher binding than the positive control sequence. More interestingly, the highest-performing sequences appeared in a range of selection rounds; although the highest intensity sequence was not observed until R4 (dark blue line), 6 out of the 8 sequences that exceed the binding performance of the positive control were observed in R2. Within the sequences that bind above background but below the positive control (i.e., with moderately high binding affinity), sequences appeared as early as R1. These results suggest that N2A2 analysis may allow discovery of high-performing aptamers with fewer rounds of selection than traditional techniques.

N2A2 Analysis of Non-Natural DNA Aptamers for VEGF

We next used click chemistry to modify the existing natural DNA sequences with non-natural base chemistry. Specifically, we used the N2A2 to generate non-natural DNA clusters directly on the flow cell, by replacing the normal deoxythymine (dT) in each sequence with a modified deoxyuracil (dU) base containing an alkyne click handle which could subsequently be functionalized with the desired chemical modification. As chemical modifications, we used the amino acids Tyrosine and Tryptophan, each purchased from a commercial source with an azide modification to enable the click reaction. During the second read of sequencing on the N2A2, software modifications allowed us to introduce the click reaction reagents (CuSO$_4$/THPTA, NaAsc and azide modification) to the flow cell, generating non-natural DNA clusters in which each "T" in the sequences was replaced with a click-modified non-natural base. We performed one experiment to generate tryptophan-modified DNA, and a separate experiment to generate tyrosine-modified DNA. For each experiment, after non-natural cluster generation, we proceeded with the VEGF fluorescence binding assay in the same manner as described above, but for lower concentration ranges due to the enhanced affinity of tryptophan and tyrosine for VEGF compared to natural DNA alone. The results of these binding assays are shown in FIG. 14, with the same color coding scheme as FIG. 13.

Figure 14:
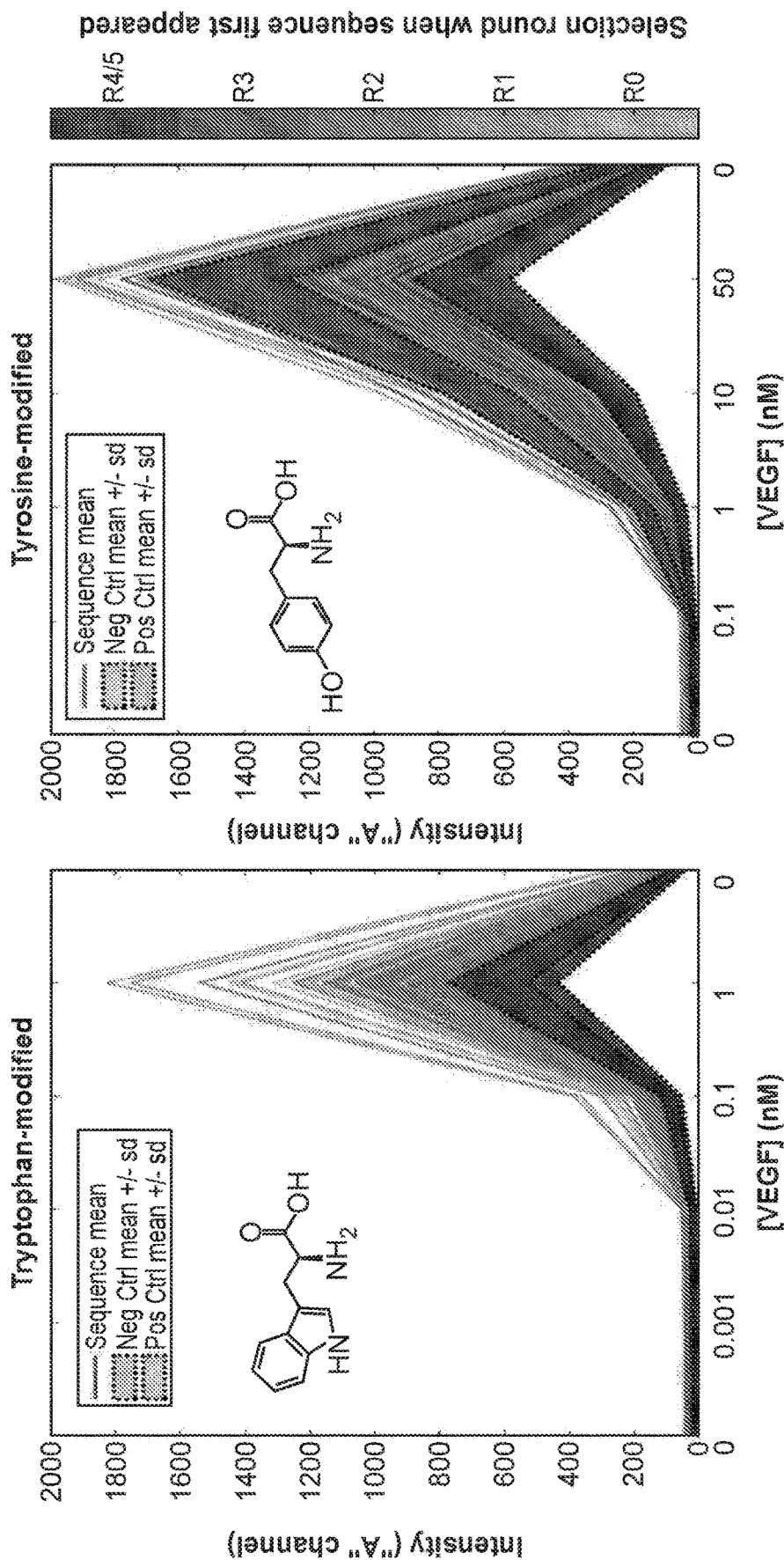
FIG. 14: VEGF-binding analysis of non-natural DNA aptamer pools with two different modified bases.

The analysis shown in FIG. 14 reveals that binding of VEGF to non-natural DNA aptamers is significantly enhanced compared to natural DNA, and that binding behavior is sequence- and modification-dependent. First, the two modifications show significantly elevated nonspecific background binding to VEGF, as shown the by the high intensity of the negative control sequence with both modifications. Second, the two modifications impact the binding of the positive control sequences in different ways; while the tryptophan modification causes the positive control to bind barely above background levels, the tyrosine modification causes a significant enhancement in binding affinity and intensity compared to the natural DNA positive control sequence, even though the sequence is identical. Third, compared to natural DNA, a much larger number of sequences is observed to bind to VEGF above background levels, with ~4× higher intensity observed compared to the best observed natural DNA aptamer. Fourth, as shown by the high number of yellow, olive, and green-colored lines in both panels, the DNA sequences that bind well to VEGF upon non-natural modification appeared very early in the selection process, some appearing in R0 (yellow lines) before any particle display was performed. This suggests that it may be possible to generate and discover high-affinity non-natural aptamers with minimal rounds of selection, which would significantly increase the speed of aptamer discovery compared to the state of the art.

Figure 15:
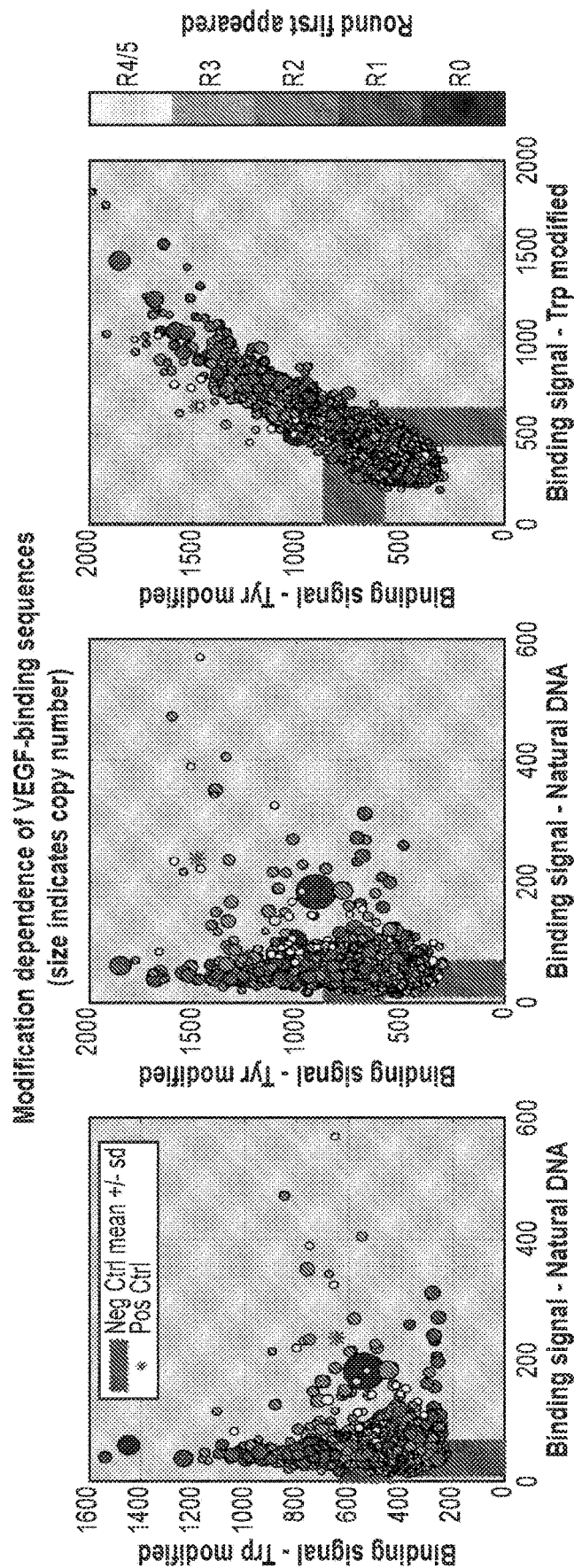
FIG. 15: Comparison of aptamer binding performance with varying modifications.

Finally, to directly compare the performance of natural DNA vs different modifications on a sequence-by-sequence basis, we plotted the mean intensity at the highest VEGF concentration from each of the three experiments for each individual sequence (FIG. 15). Each circle represents a single sequence, with the x- and y-coordinates corresponding to the binding intensities for two of the three different experiments (all three combinations are shown in separate plots). The circles are color coded according to the selection round in which they first appeared (note that the scales is flipped relative to FIGS. 13 and 14), and the circle size corresponds to the sequence's copy number on the flow cell in order to give a sense of how relatively enriched or low-abundance each sequence is. This analysis reveals that different sequences respond to modification in different ways. For instance, the binding performance of a natural aptamer and the same aptamer with either of the two different modifications is not highly correlated (left two plots), showing that the highest performing natural aptamers (right-most circles in the two left plots) are not necessarily the highest-performing modified aptamers, and vice versa. In contrast, as shown in the plot on the right, the binding for a given sequence with the two different modifications is highly correlated, although certain outlier sequences appear to bind better with one modification compared to the other. These plots show the depth of analysis possible with the N2A2 system.

Example 7—N2A2 Analysis of Non-natural DNA Aptamers for Cocaine

Figure 16:
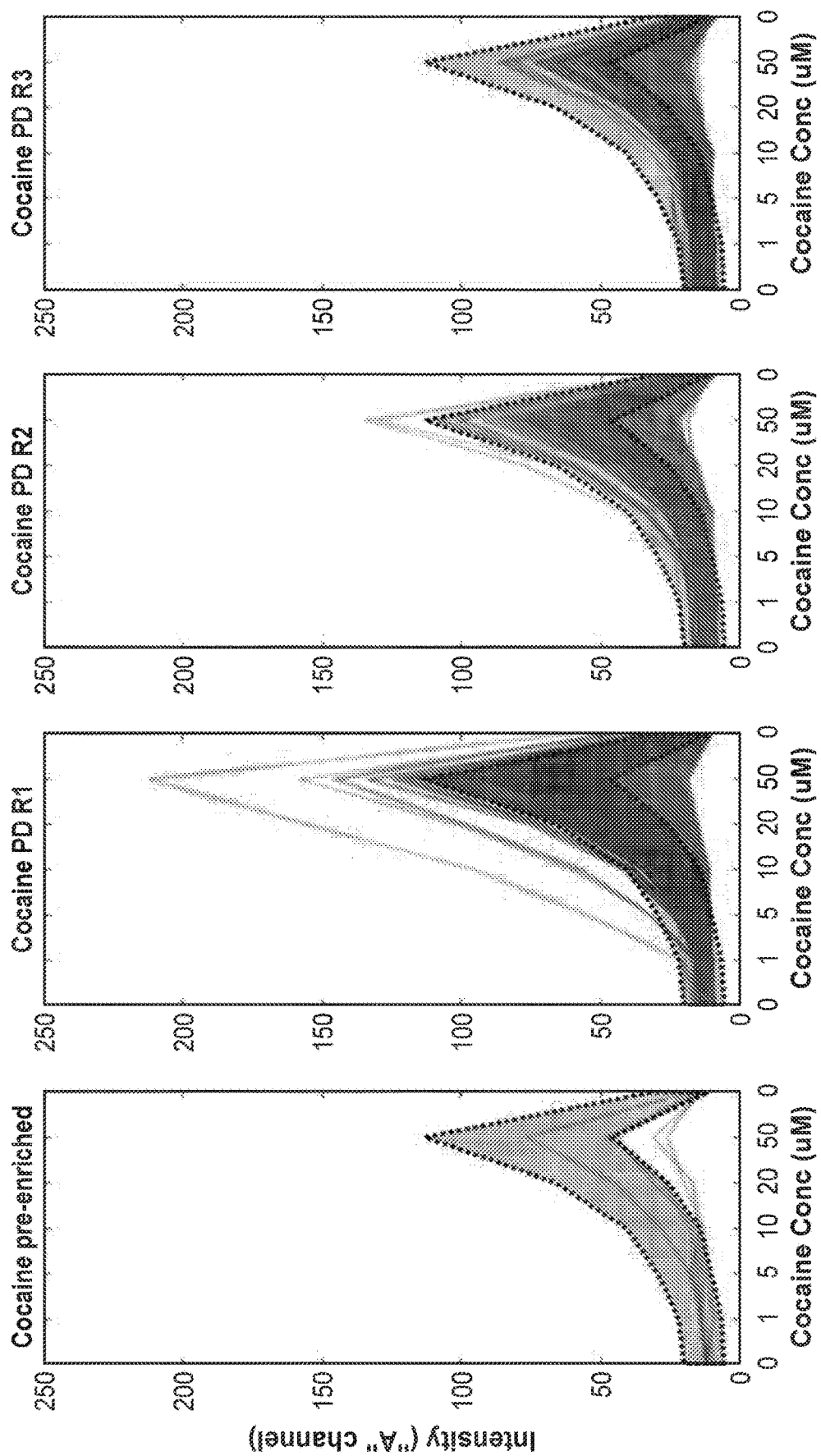
FIG. 16: Binding of a non-natural DNA aptamer pool to the small-molecule drug cocaine.

To show that the N2A2 can be used to discover non-natural DNA aptamers for small molecule targets in addition to proteins, we used the N2A2 to evaluate the binding of DNA aptamer pools selected against the drug cocaine. Similarly to the VEGF experiment described above, the aptamer pools from four different rounds of selection (one round of SELEX pre-enrichment, and three rounds of PD) were sequenced and modified with Tyrosine on the N2A2 and subsequently exposed to fluorescently-labeled cocaine. FIG. 16 shows the results of this binding assay in the same manner as plots 1 and 2, except the lines corresponding to each sequence are not color-coded by round but rather the sequences appearing in each round are plotted in separate panels. The blue shaded area shows the average+/−standard deviation of all clusters with a negative control sequence that does not bind to cocaine. Although high background binding to the negative control sequence was observed, a number of high-affinity binders were observed in the R1 and R2 pools. These data show the potential of the N2A2 to be used for analysis of molecular targets beyond proteins.

Example 8—N2A2 Enables Screening for High Specificity

N2A2 also enables isolation of high-specificity aptamers by the screen directly in complex media. As a described herein, experiments were performed to isolate a highly specific non-natural aptamer for insulin. Based on the crystal structure of the insulin receptor, key phenylalanine (F) side-chains with prominent roles in the hydrophobic pocket of the receptor binding site were identified and chosen for the screen. After performing three rounds of conventional SELEX and one round of particle display as pre-enrichment, N2A2 screen was performed with F-modified library (see methods).

To identify high-specificity aptamers, the N2A2 screen was performed in buffer and 1% human serum to identify aptamers that retain its binding affinity in serum. Briefly, the intensity of clusters at 1, 10 and 25 µM insulin in buffer and in 1% human serum (FIGS. 18A and 18B) was measured. Of the 2×10$^6$ insulin aptamer candidates screened, only 285 unique sequences showed comparable binding signal in buffer and serum. FIG. 19A shows the performance (fluorescence intensity) of each unique sequence in buffer (circle) and in serum (squares). The sequences which did not show signal above the background (below 30 a.u.) were disregarded. The sequences which performed within 10 fluorescence units under both conditions (red and blue) were highlighted as specific. Sequences which had decreased performance in serum were colored gray.

Figure 20:
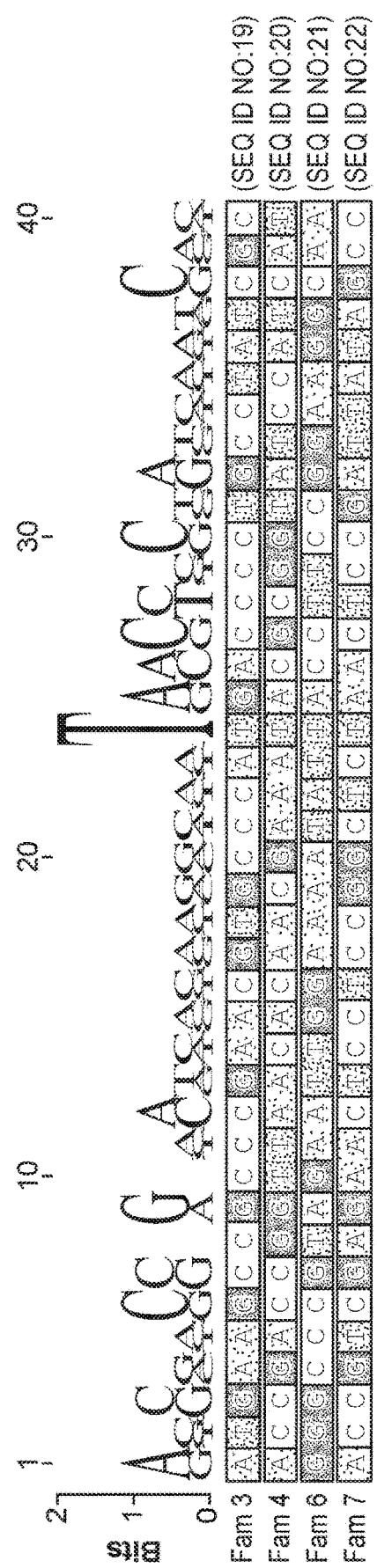
FIG. 20: Sequence logo of the top four families identified to be specific via measurement on N2A2. Below are the consensus sequences for the top four families. Position 23 has the phenylalanine modification in all four families, however the families do not have other motifs in common.

The sequences which passed the specificity criteria were aligned and clustered by family (See Methods & FIG. 20). The consensus sequences of the four largest families and six smaller families were examined by flow cytometry. Each sequence was tested at 1 µM insulin in buffer and serum (data not shown), and the sequence with the highest fluorescent signal, ins24, was characterized further.

Yoshida et al. have previously selected a DNA aptamer for insulin (IGA3) [48], but we determined that this aptamer exhibits only modest affinity, with a Kd of 12.7 µM as measured by flow cytometry. Candidate ins24 and the previously-published aptamer IGA3 were tested in a bead-based fluorescence assay under buffer conditions and measured Kds of 2.56 µM and 12.7 µM, respectively (FIG. 19B). In an identical assay in 1% serum, however, only ins24 retained meaningful binding, with a Kd of 4.8 µM (FIG. 19B). We were unable to obtain a meaningful Kd measurement for the published aptamer IGA3 in the same conditions. As demonstrated, N2A2 has allowed us to directly screen for specificity of binding in the presence of a complex background, without the need to perform positive and negative selections. One can simply measure which sequences bind to many proteins in serum and which sequences only bind to the target of interest.

Example 9—Experimental Methods

General Methods

All DNA oligonucleotides were purchased from Integrated DNA Technologies.

Primers were ordered with standard desalting. PCR templates were ordered with PAGE purification. Other than the exceptions noted below, all commercially available reagents and lab supplies were purchased from Sigma-Aldrich or Thermo Scientific. VEGF was purchased from R&D Systems. Serum was purchased from Innovative Research Inc. Insulin AF647 labelled was purchased from Nanocs. Miseq 150 V3 kits were purchased from Illumina. C8-alkyne-dUTP was purchased from IBA Life Sciences. Tyrosine azide, tryptophan azide and phenylalanine azide were purchased from ChemPeP, Inc. ECOR1 enzyme was purchased from NEB. KOD XL was purchased from Milipore Sigma. Flow cytometry assays were performed using a BD Accuri C6 flow cytometer. Fluorescence-based sorting of particles was done using a BD FACSAria II.

introduce air during cleaning cycles, but it is not used during sequencing. The fluidic line is linked to the external multiport. During an N2A2 run, our software modifications trigger the external multiport to switch ports, so the appropriate reagent is drawn into the flowcell.

Software Modification of Miseq

Two software modifications were made to the Miseq to perform our N2A2 experiment and control the external hardware.

TABLE 1

DNA sequences used in the experiments

| Sequence/ Pool Name | Sequence 5'-3' |
|---|---|
| k FP adap | TCG TCG GCA GCG TCA GAT GTG TAT AAG AGA CAG HNN NNN NNN NAG CAG CAC AGA GGT CAG ATG (SEQ ID NO: 1) |
| k RP adap | GTC TCG TGG GCT CGG AGA TGT GTA TAA GAG ACA GGA ATT CTT CAC GGT AGC ACG CAT AGG (SEQ ID NO: 2) |
| K SL2-B | AGC AGC ACA GAG GTC AGA TGA ATT GGG CCC GTC CGT ATG GTG GGT CCT ATG CGT GCT ACC GTG AA (SEQ ID NO: 3) |
| Fiducial Mark | ACC GAC GGA ACG CCA AAG AAA CGC AAG G (SEQ ID NO: 4) |
| Negative Control | TCG TCG GCA GCG TCA GAT GTG TAT AAG AGA CAG HNN NTG GAG CTT GGA TTG ATG TGG TGT GTG AGT GCG GTG CCC GAA TTC CTG TCT CTT ATA CAC ATC TCC GAG CCC ACG AGA C (SEQ ID NO: 5) |
| SL2B bt | /5Biosg/CAA TTG GGC CCG TCC GTA TGG TGG GT (SEQ ID NO: 6) |
| IGA3 bt | /5biosg/GG TGG TGG GGG GGG TTG GTA GGG TGT CTT C (SEQ ID NO: 7) |
| VEGF Selection | |
| ab FP | CCT CTC TAT GGA CAC ACT ACC CT (SEQ ID NO: 8) |
| ab RP | CTG CAC TGC GTT CCT GAT ACC CT (SEQ ID NO: 9) |
| T14_15 | CCT CTC TAT GGA CAC ACT ACC CTC CCA GTA GGG TGG CAG TCA GGG AGT ACA TAA GGG TAT CAG GAA CGC AGT GCA G (SEQ ID NO: 10) |
| Insulin Selection | |
| ar FP | GCG CAT ACC AGC TTA TTC AAT T (SEQ ID NO: 11) |
| ar RP | GCC GAG ATT GCA CTT ACT ATC T (SEQ ID NO: 12) |
| Ins24 | GCG CAT ACC AGC TTA TTC AAT CGT CGA GAA CTC CTC CGG CTC TAA CTC CGA TTA TAG CCA AAG ATA GTA AGT GCA ATC TCG GC (SEQ ID NO: 13) |
| ar FP-adap | TCG TCG GCA GCG TCA GAT GTG TAT AAG AGA CAG HNN NGC GCA TAC CAG CTT ATT CAA TT (SEQ ID NO: 14) |
| ar RP-adap | GTC TCG TGG GCT CGG AGA TGT GTA TAA GAG ACA GGA ATT CGC CGA GAT TGC ACT TAC TAT CT (SEQ ID NO: 15) |

Hardware Modification of Miseq

A minor modification was made to a standard Illumina Miseq to accommodate the additional reagents we wanted to introduce to the flowcell during the binding experiments. Compatible tubing, couplers and a multiport were obtained from a defunct Illumina GAII. A fluidic inlet line was added to an unused position (port 23) in the instrument's internal multiport (Valco Instruments Co Inc). Port 23 is used to First, we modified the run configuration files to perform a custom set of chemistry steps after sequencing, enabling us to automatically perform custom chemical incorporation and binding assays. The custom chemistry definitions include pumping KODXL enzyme, EcoR1 enzyme or buffer from the additional ports in the Miseq cartridge, heating the flowcell, incubating reagents on the flowcell, and pumping protein dilutions from the external reagents through the external multiport.

Second, to control the external multiport, we use a free software, FolderAgent, which monitors the temporary experiment folder and triggers commands upon the creation of .cif files as they are processed. During the second read, first cycle, the EcoR1 site is cleaved. The flow cell is washed with buffer and NaOH. Depending on whether we are performing a non natural run or natural DNA run, the flowcell will be incubated with the click reagents or wash buffer for 40 minutes, then washed again. Decision Tree A switches the multiport to the NaOH port after the buffer wash. During the second read, second cycle, which is the first in situ binding measurement, Decision Tree B commands the multiport to switch to the NaOH port during the wash step, start a timer, display "Target Incubation", check the cycle number and change the multiport to the correct target port. The cycle number and target ports are customized for each individual experiment. Additional documentation can be provided upon request.

CuAAC Chemistry on the Miseq

We utilized the paired end turnaround procedure of the standard Miseq workflow to introduce the new nucleobases that allow us to convert natural DNA into non-natural aptamers on the flow cell. We introduced a commercially available polymerase, KodXL, and a new dNTP mix, including C8-alkyne-dUTP, into user-replaceable reagent tubes in the Miseq reagent cartridge. The new PCR mix consists of: 804 ul water, 100 ul 10× KOD buffer, 20 ul dATP (10 mM), 20 ul dGTP (10 mM), 20 ul dCTP (10 mM), 20 ul c8-alk-dUTP (10 mM) and 16 ul KOD XL. During the paired end turnaround, instead of using the standard amplification master mix, the sequence recipe was edited to use the KodXL PCR mix, which was stored in the reagent cartridge.

During the click step, reagents were prepared 30 minutes before the Miseq was commanded to draw the sample. Pre-prepared 0.1 M $CuSO_4$/0.2 M THPTA in $H_2O$ and 10 mM azide functional group (W, Y or F) were degassed with N2 for at least 15 minutes. 20 mg of sodium ascorbate was measured out and resuspended in 1 mL $H_2O$ directly before the command. 25 ul NaAsc was added to the click reaction and the tube was immediately attached to the external port of the Miseq. The final concentration of $CuSO_4$/THPTA was 1.5 mM, azide functional group was 0.2 mM and NaAsc was 5 mM. The alkynes present in the oligos on the flowcell surface which had been incorporated by the KODXL PCR mix were the limiting reagent.

Validating Conversion to Non-Natural Aptamers

To validate the complete generation of the non-natural DNA strand, we incubated the strand with a fluorophore labelled fiducial mark. If the turnaround was unsuccessful with the new polymerase, the fiducial mark would not appear on the flowcell. Our test shows that the C8-alkyne-dUTP incorporation was successful.

New functional groups are introduced to our non-natural DNA strands through use of a copper click reaction, so in order to validate our reaction procedure on the flowcell, we introduced a cy3 labelled azide. The appearance of clusters during the second read indicate that our reaction was successful.

Protein Labeling

VEGF protein was resuspended in 0.05M sodium borate buffer and incubated with Dylight 650 NHS ester (ThermoFisher 62265) for 1 hour. Non reacted reagent was removed by dialysis. Degree of protein labelling was determined using NanoDrop. The Dylight 650 fluorophore was chosen because it aligns with the "A" and "C" imaging channels on the MiSeq. Insulin was purchased labelled with AF647.

SELEX and Particle Display

VEGF: One round of regular SELEX was performed with VEGF on particles. Aptamer beacon particle display was used to further enhance the affinity and structure switching properties of the library. In rounds one and two, particle display was used to screen for affinity binders, and no screen for refolding was performed. In the subsequent rounds three through five, both binding and refolding screens were performed, with decreasing concentrations of protein used each time. The screening was ended when no further improvement was seen in binding between round 4 and round 5 binding assays.

Figure 22:
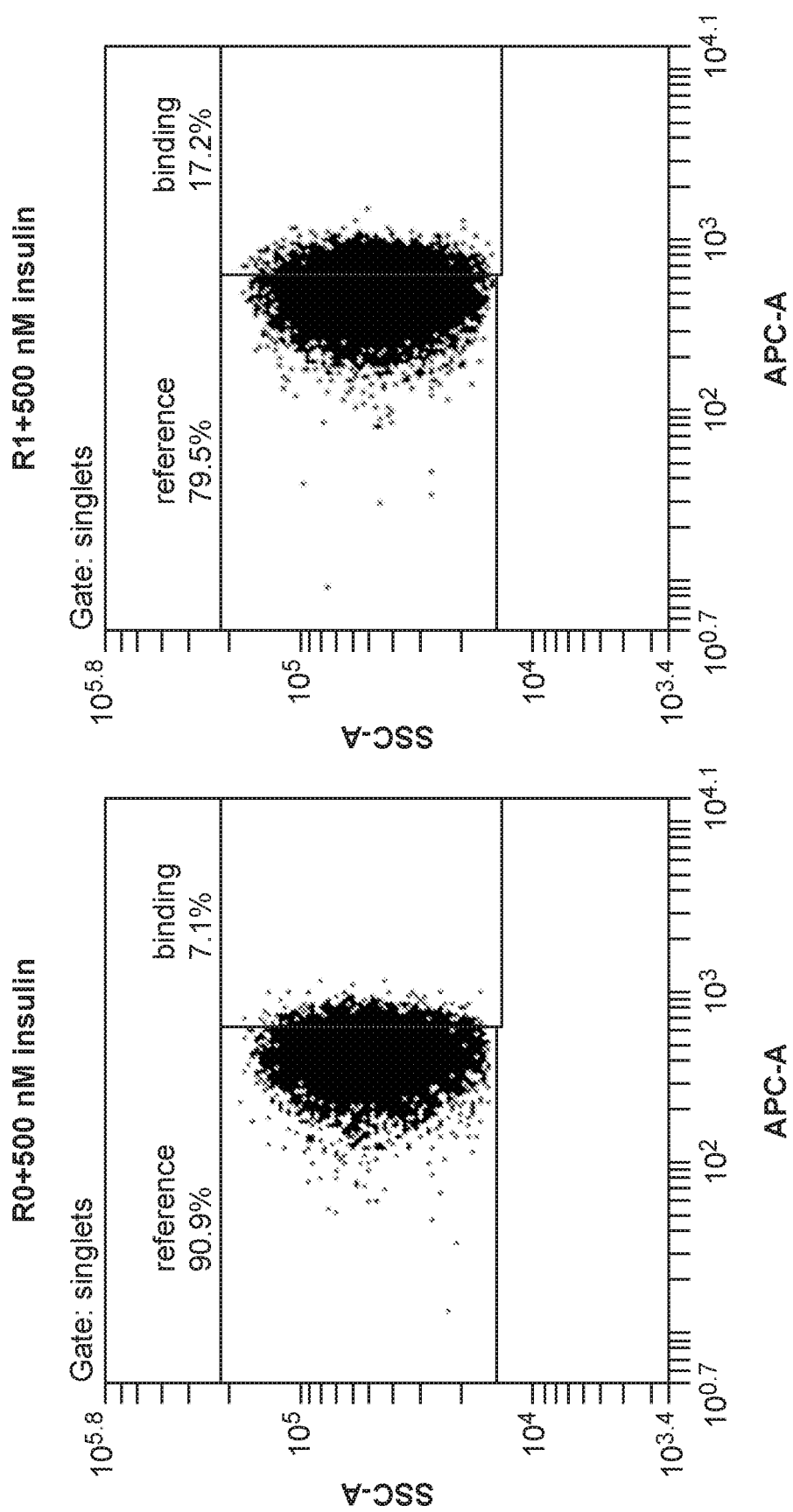
FIG. 22: Flow cytometry analysis of R0 phenylalanine modified DNA particles binding to AF647 insulin (left). After the first round of FACS (right), the percentage of the binding population increased by 10%.

Insulin: Three rounds of SELEX with natural DNA was performed with bead imobbilized insulin. Next, we completed 2 rounds of PD with phenylalanine-modified DNA against Alexa Fluor 647-labled insulin. After one round of PD we observe a 2.5-fold increase in the percentage of aptamer particles binding at a concentration of 500 nM insulin (FIG. 22). High-throughput sequencing results revealed that our library had significantly converged after PD, with the round 2 library containing only 12% unique sequences.

DNA Preparation for High Throughput Sequencing

We prepared the pools of DNA from SELEX and PD for sequencing and binding analysis on the N2A2 via attachment of custom sequencing adapters (Table S1) and Nextera XT indices (Illumina). The additional sequences were attached via 4-8 rounds of PCR and then gel purified. DNA was quantified via qPCR.

N2A2 VEGF Data Collection

The same input DNA stocks and labeled VEGF protein were used for all three experiments, but new sequencing cartridges and flow-cells were used for each experiment. For the natural DNA experiment, natural dNTPs were used during the paired end turnaround but the sequence was still cleaved at the ECOR1 cleavage site before labelled VEGF was introduced. During the non-natural conversion process, either tyrosine-azide or tryptophan-azide was clicked onto the alkyne handle and then the sequence was cleaved. After collecting the sequence information, we exposed the aptamer libraries to fluorophore labelled VEGF at concentrations of 1 nM, 10 nM, 50 nM and 100 nM.

We first identified the copy number for each sequence on the flow-cell. We restricted our analysis to sequences with >10 copies on the flow-cell to ensure an adequate number of replicates and minimize noise. For each of these sequences, we averaged the fluorescence intensity of all clusters with that sequence at each VEGF concentration To give a sense of background binding as well as the typical variability in intensity data for "dark" clusters with the same sequence, the binding of the negative control sequence is plotted as the grey shaded region, which covers the mean intensity+/−one standard deviation across all clusters with this sequence. To show the magnitude and variability of a "true" binding sequence, we plotted the data for all clusters matching the positive control sequence as the red shaded region, which covers the mean intensity+/−one standard deviation across all clusters with this sequence.

Figures 21A, 21B, 21C:
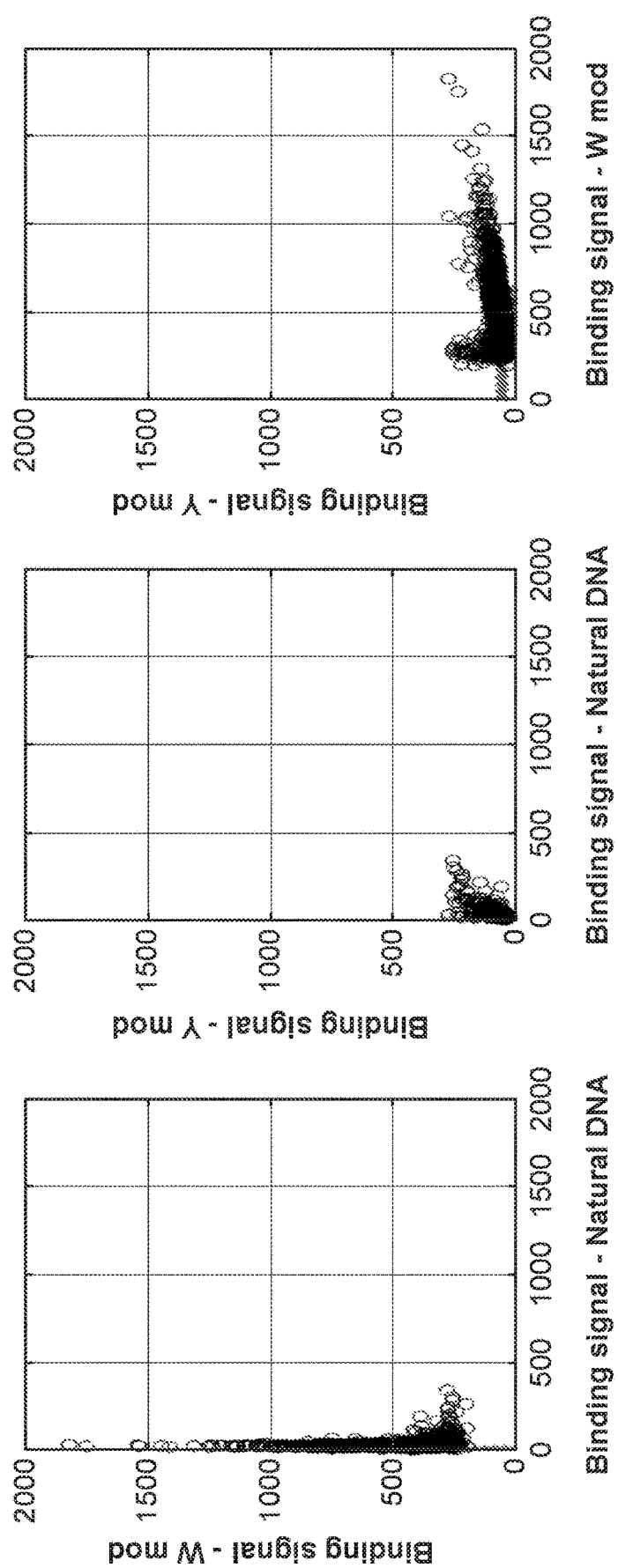
FIGS. 21A-21C: Binding signal of sequences tested in the tyrosine (Y) and tryptophan (W) N2A2 experiments at 1 nM VEGF.

Our first tryptophan modified DNA experiment with similar concentrations of VEGF (1 nM to 100 nM) was oversaturated with signal, so we reduced the VEGF concentration range to 1 pM to 1 nM VEGF Cross Reference Analysis We subsequently subjected these non-natural aptamer pools to closer evaluation to compare the effects of different modifications on a sequence-by-sequence basis. We evaluated the performance of every sequence which appeared in the three experiments. At 1 nM VEGF, most of the sequences that show high intensity of binding with the tryptophan modification do not exhibit meaningful binding when they instead incorporate the tyrosine modification (FIGS. 21A-21C).

Insulin Family Analysis

Figures 18A, 18B:
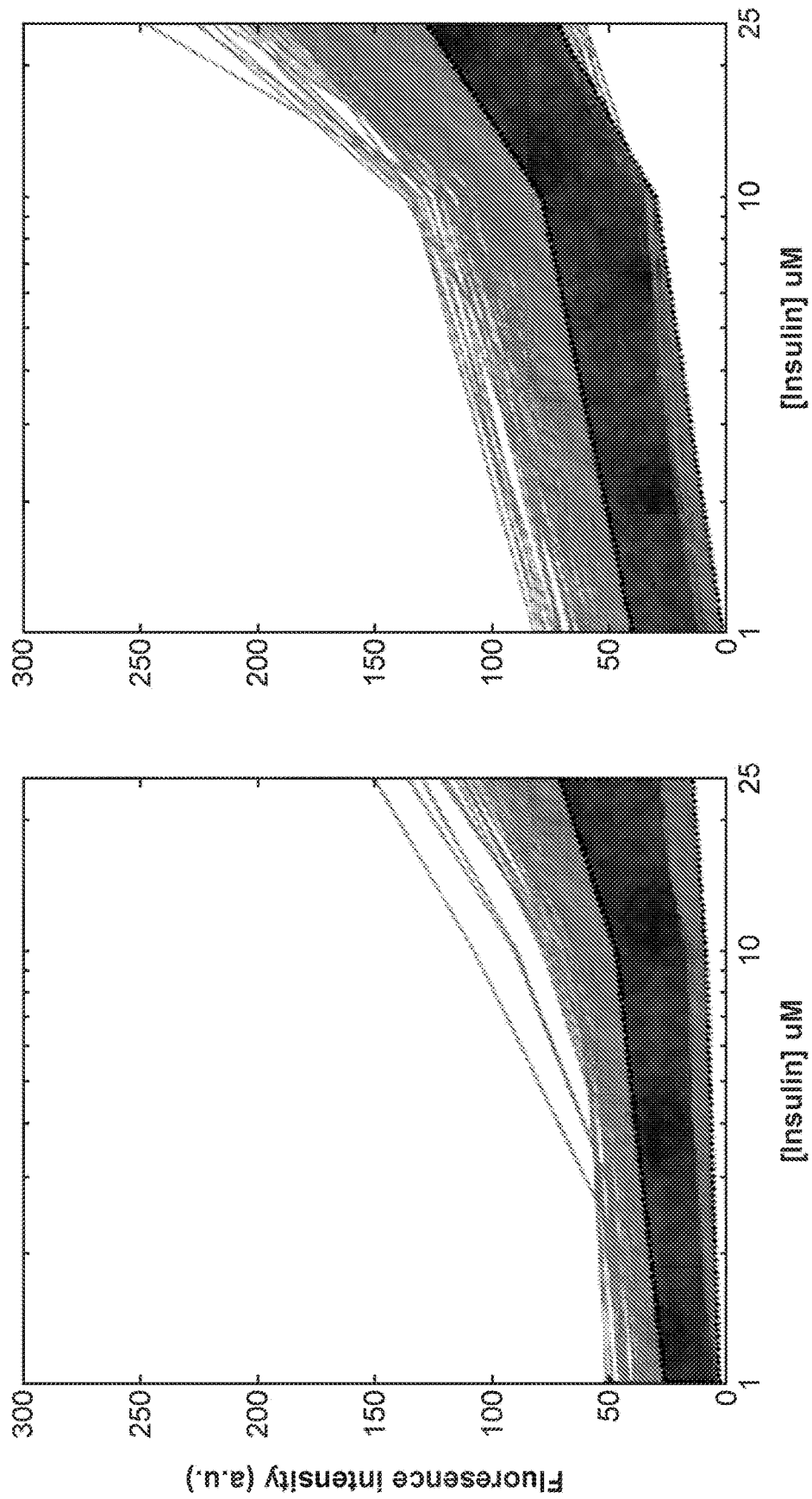
FIGS. 18A and 18B: N2A2 produces high-specificity non-natural DNA aptamers.

The same data collection and processing method as the VEGF experiments was used for the insulin experiments. FIGS. 18A and 18B shows the raw binding curves obtained from the experiment in buffer and serum.

These sequences were aligned using a progressive alignment method and Gonnet scoring matrix (Gap open penalty=30, Gap extension penalty=5). The aligned sequences were clustered into families, groups of sequences with single or double point mutations, using k-means clustering (Bin=10). 285 specific sequences fell into four main families. Specific sequences which did not fall into a major family were clustered again using k-means clustering (Bin=100). Five of the smaller families (<50 sequences) were also chosen for further testing.

FIG. 20 shows the sequence logo for the four families and the individual consensus sequence for each family. It is interesting to note that families 3,4, and 6 have only six modifications (indicated by the green 'T') and family 7 has seven. If the phenylalanine is adding to the affinity of the aptamer candidate, we would expect there to be more modifications. However, the forward and reverse primer complement of this library has a high T content, so the affinity may come from the primers. Position 23 in the sequence logo is a phenylalanine modification in all the families and could play an important role in insulin recognition.

Binding Assay by Flow Cytometry

We performed PCR with natural DNA sequences, forward primer-coated beads, and a master mix which included the non-natural dNTP. We used click chemistry to introduce the tyrosine, tryptophan or phenylalanine modification, and then generated monoclonal, single-stranded modified aptamer beads. These samples were incubated with a variety of concentrations of VEGF or insulin for 40 minutes, washed twice with cold buffer, after which fluorescence was measured by flow cytometry.

REFERENCES

[1] G. Smith, "Filamentous fusion phage: Novel expression vectors that display cloned antigens on the virion surface," Science, vol. 228, no. 4705, pp. 1315-1317, 1985.

[2] G. Chao, W. L. Lau, B. J. Hackel, S. L. Sazinsky, S. M. Lippow, and K. D. Wittrup, "Isolating and engineering human antibodies using yeast surface display," Nat. Protoc., vol. 1, no. 2, pp. 755-68, January 2006.

[3] R. Roberts, and J. Szostak, "RNA-peptide fusions for the in vitro selection of peptides," Proc. Natl. Acad. Sci., vol. 94, no. 23, pp. 12297-12302, 1997.

[4] J. Wang, Q. Gong, N. Maheshwari, M. Eisenstein, M. L. Arcila, K. S. Kosik, and H. T. Soh, "Particle display: A quantitative screening method for generating high affinity aptamers," Angew. Chemie, vol. 126, pp. 1-6, 2014.

[5] F. Pfeiffer, M. Rosenthal, and J. Siegl, "Customised nucleic acid libraries for enhanced aptamer selection and performance," Curr. Opin. Biotechnol., vol. 48, pp. 111-118, 2017.

[6] J. C. Rohloff, A. D. Gelinas, T. C. Jarvis, U. A. Ochsner, D. J. Schneider, L. Gold, and N. Janjic, "Nucleic acid ligands with protein-like side chains: Modified aptamers and their use as diagnostic and therapeutic agents.," Mol. Ther. Nucleic Acids, vol. 3, p. e201, January 2014.

[7] V. B. Pinheiro, A. I. Taylor, C. Cozens, M. Abramov, M. Renders, S. Zhang, J. C. Chaput, J. Wengel, S.-Y. Peak-Chew, S. H. McLaughlin, P. Herdewijn, and P. Holliger, "Synthetic genetic polymers capable of heredity and evolution.," Science, vol. 336, no. 6079, pp. 341-4, April 2012.

[8] V. B. Pinheiro, A. I. Taylor, C. Cozens, M. Abramov, M. Renders, S. Zhang, J. C. Chaput, J. Wengel, S.-Y. Peak-Chew, S. H. McLaughlin, P. Herdewijn, and P. Holliger, "Synthetic genetic polymers capable of heredity and evolution," Science, vol. 336, pp. 341-345, 2012.

[9] M. Kimoto, R. Yamashige, K. Matsunaga, S. Yokoyama, and I. Hirao, "Generation of high-affinity DNA aptamers using an expanded genetic alphabet.," Nat. Biotechnol., vol. 31, no. 5, pp. 453-7, May 2013.

[10] S. Diafa and M. Hollenstein, "Generation of aptamers with an expanded chemical repertoire," Molecules, vol. 20, no. 9, pp. 16643-16671, 2015.

[11] S. E. Lupold, B. J. Hicke, Y. Lin, and D. S. Coffey, "Identification and characterization of nuclease-stabilized RNA molecules that bind human prostate cancer cells via the prostate-specific membrane antigen," Cancer Res., vol. 62, pp. 4029-4033, 2002.

[12] M. C. Culbertson, K. W. Temburnikar, S. P. Sau, J. Liao, S. Bala, and J. C. Chaput, "Evaluating TNA stability under simulated physiological conditions," Bioorg. Med. Chem. Lett., vol. 26, no. 10, pp. 2418-2421, 2016.

[13] G. Zhu, M. Ye, M. J. Donovan, E. Song, Z. Zhao, and W. Tan, "Nucleic acid aptamers: an emerging frontier in cancer therapy," Chem. Commun. (Camb)., vol. 48, no. 85, pp. 10472-80, November 2012.

[14] D. A. Malyshev, K. Dhami, H. T. Quach, T. Lavergne, P. Ordoukhanian, A. Torkamani, and F. E. Romesberg, "Efficient and sequence-independent replication of DNA containing a third base pair establishes a functional six-letter genetic alphabet," Proc. Natl. Acad. Sci., vol. 109, no. 30, pp. 12005-12010, 2012.

[15] J. Wang, J. Yu, Q. Yang, J. Mcdermott, A. Scott, M. Vukovich, R. Lagrois, Q. Gong, W. Greenleaf, M. Eisenstein, B. S. Ferguson, and H. T. Soh, "Multiparameter particle display (MPPD): A quantitative screening method for the discovery of highly specific aptamers," Angew. Chemie Int. Ed. vol. 94305, pp. 744-747, 2017.

[16] W. H. Thiel, T. Bair, A. S. Peek, X. Liu, J. Dassie, K. R. Stockdale, M. a Behlke, F. J. Miller, and P. H. Giangrande, "Rapid identification of cell-specific, internalizing RNA aptamers with bioinformatics analyses of a cell-based aptamer selection.," PLoS One, vol. 7, no. 9, p. e43836, January 2012.

[17] S. S. Oh, J. Qian, X. Lou, Y. Zhang, Y. Xiao, and H. T. Soh, "Generation of highly specific aptamers via micromagnetic selection," Anal. Chem., vol. 81, no. 13, pp. 5490-5, July 2009.

[18] L.-Y. Hung, C.-H. Wang, K.-F. Hsu, C.-Y. Chou, and G.-B. Lee, "An on-chip Cell-SELEX process for automatic selection of high-affinity aptamers specific to different histologically classified ovarian cancer cells," Lab Chip, August 2014.

[19] A. Cibiel, N. N. Quang, K. Gombert, B. Theze, A. Garofalakis, and F. Duconge, "From ugly duckling to swan: unexpected identification from cell-SELEX of an anti-Annexin A2 aptamer targeting tumors," PLoS One, vol. 9, no. 1, p. e87002, January 2014.

[20] K.-M. Song, S. Lee, and C. Ban, "Aptamers and their biological applications," Sensors (Basel)., vol. 12, no. 1, pp. 612-31, January 2012.

[21] C. B. Chen, K. R. Dellamaggiore, C. P. Ouellette, C. D. Sedano, M. Lizadjohry, G. A. Chernis, M. Gonzales, F. E. Baltasar, A. L. Fan, R. Myerowitz, and E. F. Neufeld, "Aptamer-based endocytosis of a lysosomal enzyme," Proc. Natl. Acad. Sci. U.S.A, vol. 105, no. 41, pp. 15908-13, October 2008.

[22] Q. Gong, J. Wang, K. M. Ahmad, A. T. Csordas, J. Zhou, J. Nie, R. Stewart, J. a Thomson, J. J. Rossi, and H. T. Soh, "Selection strategy to generate aptamer pairs that bind to distinct sites on protein targets," Anal. Chem., vol. 84, no. 12, pp. 5365-71, June 2012.

[23] F. Tolle, G. M. Brandle, D. Matzner, and G. Mayer, "A Versatile Approach Towards Nucleobase-Modified Aptamers," Angew. Chemie—Int. Ed., vol. 54, no. 37, pp. 10971-10974, 2015.

[24] R. Nutiu and Y. Li, "In vitro selection of structure-switching signaling aptamers," Angew. Chemie—Int. Ed., vol. 44, no. 11, pp. 1061-1065, 2005.

[25] J. M. Tome, A. Ozer, J. M. Pagano, D. Gheba, G. P. Schroth, and J. T. Lis, "Comprehensive analysis of RNA-protein interactions by high-throughput sequencing-RNA affinity profiling," Nat. Methods, vol. 11, no. 6, pp. 683-8, 2014.

[26] J. D. Buenrostro, C. L. Araya, L. M. Chircus, C. J. Layton, H. Y. Chang, M. P. Snyder, and W. J. Greenleaf, "Quantitative analysis of RNA-protein interactions on a massively parallel array reveals biophysical and evolutionary landscapes," Nat. Biotechnol., vol. 32, no. 6, pp. 562-8, 2014.

[27] Kaur, H. and Yung, L.-Y. L. "Probing high affinity sequences of DNA aptamer against VEGF165," PLoS One, vol. 7, no. 2, p. e31196, 2012.

[28] Hasegawa, H., Sode, K. and Ikebukuro, K. "Selection of DNA aptamers against VEGF165 using a protein competitor and the aptamer blotting method," Biotechnol. Lett. vol. 30, no. 5, pp. 829-34, 2008.

[29] J. Y. Kim, Y. Kim, and G. M. Lee, "CHO cells in biotechnology for production of recombinant proteins: current state and further potential," pp. 917-930, 2012.

[30] D. P. Morse, "Direct selection of RNA beacon aptamers," Biochem. Biophys. Res. Commun., vol. 359, pp. 94-101, 2007.

[31] S. G. Trevino and M. Levy, "High-throughput bead-based identification of structure-switching aptamer beacons.," Chembiochem, vol. 15, no. 13, pp. 1877-81, September 2014.

[32] R. Stoltenburg, N. Nikolaus, and B. Strehlitz, "Capture-SELEX: Selection of DNA aptamers for aminoglycoside antibiotics," J. Anal. Methods Chem., vol. 2012, 2012.

[33] F. Pfeiffer and G. Mayer, "Selection and biosensor application of aptamers for small molecules," Front. Chem., vol. 4, no. June, pp. 1-21, 2016.

[34] T. A. Feagin, D. P. V Olsen, Z. C. Headman, and J. M. Heemstra, "High-throughput enantiopurity analysis using enantiomeric DNA-based sensors," J. Am. Chem. Soc., vol. 137, no. 12, pp. 4198-4206, 2015.

[35] J. Ruta, S. Perrier, C. Ravelet, J. Fize, and E. Peyrin, "Noncompetitive fluorescence polarization aptamer-based assay for small molecule detection," vol. 81, no. 17, pp. 7468-7473, 2009.

[36] S. Rana, "Rapid analysis of urinary opiates using fast gas chromatography—mass spectrometry and hydrogen as a carrier gas," Egypt. J. Forensic Sci., vol. 4, no. 3, pp. 100-107, 2014.

[37] B. Chen, S. Wang, and R. H. Liu, "GC-MS analysis of multiply derivatized opioids in urine," J. Mass. Spectrom. vol. 42, no. 8, pp. 1012-1023, 2007.

[38] B. McCarberg, "Chronic pain: Reducing costs through early implementation of adherence testing and recognition of opioid misuse," Postgrad. Med., vol. 123, no. 6, pp. 132-139, 2011.

[39] B. McCarberg, "A critical assessment of opioid treatment adherence using urine drug testing in chronic pain management," Postgrad. Med., no. 6, pp. 124-131, 2011.

[40] A. Manglik, A. C. Kruse, T. S. Kobilka, F. S. Thian, J. M. Mathiesen, and R. K. Sunahara, "Crystal structure of the mu-opioid receptor bound to a morphinan antagonist," Nature, vol. 485, pp. 321-327, 2012.

[41] H. Qu, A. T. Csordas, J. Wang, S. S. Oh, M. S. Eisenstein, and H. T. Soh, "Rapid and label-free strategy to isolate aptamers for metal ions," ACS Nano, vol. 10, no. 10, pp. 7558-65, 2016.

[42] D. Lee, R. Karchin, and M. A. Beer, "Discriminative prediction of mammalian enhancers from DNA sequence," Genome Res., vol. 21, no. 12, pp. 2167-2180, 2011.

[43] T. Hashimoto, R. I. Sherwood, D. D. Kang, N. Rajagopal, A. A. Barkal, H. Zeng, B. J. M. Emons, S. Srinivasan, T. Jaakkola, and D. K. Gifford, "A synergistic DNA logic predicts genome-wide chromatin accessibility," Genome Res., vol. 26, no. 10, pp. 1430-1440, 2016.

[44] C. G. Knight, M. Platt, W. Rowe, D. C. Wedge, F. Khan, P. J. R. Day, A. Mcshea, J. Knowles, and D. B. Kell, "Array-based evolution of DNA aptamers allows modelling of an explicit sequence-fitness landscape," Nucleic Acids Res., vol. 37, no. 1, pp. 1-10, 2009.

[45] D. R. Kelley, J. Snoek, and D. R. Kelley, "Basset: Learning the regulatory code of the accessible genome with deep convolutional neural networks," Genome Res., vol. 26, no. 7, pp. 990-9, 2015.

[46] M. T. Weirauch, A. Cote, R. Norel, M. Annala, Y. Zhao, T. R. Riley, J. Saez-rodriguez, T. Cokelaer, A. Vedenko, S. Talukder, D. Consortium, H. J. Bussemaker, Q. D. Morris, M. L. Bulyk, G. Stolovitzky, and T. R. Hughes, "Evaluation of methods for modeling transcription factor sequence specificity," Nat. Biotechnol., vol. 31, no. 2, pp. 126-134, 2013.

[47] A. T. Kalai and R. Sastry, "The Isotron Algorithm: High-Dimensional Isotonic Regression," in COLT, 2009.

[48] W. Yoshida, E. Mochizuki, M. Takase, H. Hasegawa, Y. Morita, H. Yamazaki, K. Sode, K. Ikebukuro, and W. Yoshida, "Selection of DNA aptamers against insulin and construction of an aptameric enzyme subunit for insulin sensing," in Biosens. Bioelectron. vol. 24, pp. 1116-1120, 2009.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for screening a library of aptamers for aptamers having binding affinity to a target molecule, comprising:
   (a) providing a solid support comprising clusters of sequence-identified adaptor end- linked aptamers, wherein each cluster comprises a plurality of identical sequence-identified adaptor end-linked aptamers comprising one or more non-natural nucleotide covalently bonded to a binding agent, and optionally extended solid support-linked oligonucleotides comprising complements of the adaptor end-linked aptamers, and wherein the sequence of the adaptor end-linked aptamers in each cluster is unique compared to that of the other clusters;
   (d) probing the clusters of adaptor end-linked aptamers linked to the solid support with a target molecule;
   (e) washing unbound target molecule from the solid support;
   (f) screening the solid support for binding and location of the target molecule; and
   (g) correlating the location of binding of the target molecule to the nucleotide sequence of an solid support-linked aptamer at the location of binding of the target molecule, thereby identifying the nucleotide sequence of an aptamer that binds the target molecule.

2. The method of claim 1, wherein the providing comprises:
   (a) hybridizing a plurality of adaptor end-linked aptamers to adaptor-complementary oligonucleotides linked to a solid support;
   (b) subjecting the hybridized adaptor end-linked aptamers to nucleotide sequencing by:
      (i) extending with a polymerase the hybridized adaptor-complementary oligonucleotide in a template-dependent manner to generate an extended solid support-linked antisense oligonucleotide whose sequence is complementary to the adaptor end- linked aptamer; and
      (ii) generating clusters of identical solid support-linked oligonucleotides having sense and antisense strands through bridge amplification;
      (iii) selectively cleaving sense oligonucleotides, leaving only antisense oligonucleotides linked to the solid support;
      (iv) sequencing by synthesis the antisense oligonucleotides; and
      (v) recording the location and nucleotide sequence of the antisense oligonucleotides linked to the solid support;
   (c) performing bridge amplification of the antisense oligonucleotides linked to the solid support in the presence of one or more non-natural nucleotide to form clusters of extended solid support-linked sense oligonucleotides and antisense oligonucleotides, thereby introducing a non-natural nucleotide into the sense oligonucleotides wherein the non-natural nucleotide comprises a functional group to form the sequence-identified adaptor end-linked aptamers;
   (d) selectively cleaving the antisense oligonucleotides from the solid support, thereby providing a solid support comprising clusters of sequence-identified adaptor end-linked aptamers.

3. The method of claim 2, wherein the non-natural nucleotide comprises an alkyne or azide functional group.

4. The method of claim 3, wherein the non-natural nucleotide comprises an alkyne functional group.

5. The method of claim 4, wherein the non-natural nucleotide is C8-alkyne-dUTP.

6. The method of claim 2, further comprising following the performing bridge amplification, modifying the non-natural nucleotide by covalently conjugating a binding agent comprising a compatible functional group to the non-natural nucleotide, wherein the compatible functional group in the binding agent and the functional group in the non-natural nucleotide react to form a modified non-natural nucleotide comprising the binding agent.

7. The method of claim 6, wherein the compatible functional group in the binding agent is an azide.

8. The method of claim 7, wherein during the modifying the azide undergoes Cu-catalyzed azide-alkyne cycloaddition (CuAAC) with the alkyne in the non-natural nucleotide to form a covalent bond.

9. The method of claim 1, wherein the binding agent is an amino acid, a sugar, a peptide, or a protein.

10. The method of claim 9, wherein the sugar is a monosaccharide or a polysaccharide.

11. The method of claim 9, wherein the peptide is a synthetic peptide.

12. The method of claim 9, wherein the protein is a synthetic protein.

13. The method of claim 1, wherein the binding agent is an azide-modified tyrosine.

14. The method of claim 1, wherein the binding agent is an azide-modified tryptophan.

15. The method of claim 1, wherein the binding agent is an azide-modified boronic acid.

16. The method of claim 1, wherein the target molecule is a peptide, a protein, a small molecule, a mixture of cellular membrane fragments, or a microorganism.

17. The method of claim 1, wherein the target molecule is labeled.

18. The method of claim 1, wherein the adaptor end-linked aptamers comprise a label and the target molecule induces a conformational change in the adaptor end-linked aptamers upon binding that alters signal from the label.

19. The method of claim 1, wherein the target molecule is in a complex mixture including non-target molecules.

20. The method of claim 1, further comprising performing a binding assay that measures binding affinity the adaptor end-linked aptamers to the target molecule.

21. The method of claim 20, wherein the binding assay is a fluorescence- based binding assay.

22. The method of claim 1, wherein the solid support comprises a polystyrene surface, a polypropylene surface, a gold surface, a glass surface, or a silicon wafer.

23. The method of claim 1, wherein the target molecule is insulin.

24. The method of claim 23, wherein the aptamer has a sequence that has at least 85% identity to the sequence of SEQ ID NO:13.

* * * * *

UNITED STATES PATENT AND TRADEMARK OFFICE
CERTIFICATE OF CORRECTION

PATENT NO. : 12,258,558 B2
APPLICATION NO. : 15/734512
DATED : March 25, 2025
INVENTOR(S) : Trevor Feagin et al.

Page 1 of 1

It is certified that error appears in the above-identified patent and that said Letters Patent is hereby corrected as shown below:

In the Claims

In Column 49, Line 6:
In Claim 1, delete "end- linked" and insert -- end-linked --.

In Column 49, Line 38:
In Claim 2, delete "end- linked" and insert -- end-linked --.

In Column 50, Line 53:
In Claim 21, delete "fluorescence- based" and insert -- fluorescence-based --.

Signed and Sealed this
Thirteenth Day of May, 2025

Coke Morgan Stewart
*Acting Director of the United States Patent and Trademark Office*